(12) United States Patent
Freishtat et al.

(10) Patent No.: US 11,320,441 B2
(45) Date of Patent: May 3, 2022

(54) ADIPOCYTE-DERIVED EXOSOMES, AND COMPOSITIONS, KITS, AND METHODS OF USING THE SAME FOR DETECTION AND SCREENING

(71) Applicant: CHILDREN'S NATIONAL MEDICAL CENTER, Washington, DC (US)

(72) Inventors: Robert J. Freishtat, Potomac, MD (US); Evan Nadler, Washington, DC (US); Monica Hubal, Indianapolis, IN (US); Sarah Ferrante, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 947 days.

(21) Appl. No.: 15/580,047

(22) PCT Filed: Jun. 10, 2016

(86) PCT No.: PCT/US2016/036880
§ 371 (c)(1),
(2) Date: Dec. 6, 2017

(87) PCT Pub. No.: WO2016/201220
PCT Pub. Date: Dec. 15, 2016

(65) Prior Publication Data
US 2018/0136230 A1    May 17, 2018

Related U.S. Application Data

(60) Provisional application No. 62/173,496, filed on Jun. 10, 2015, provisional application No. 62/336,943, filed on May 16, 2016.

(51) Int. Cl.
*G01N 33/68* (2006.01)
*G01N 33/566* (2006.01)
*G01N 33/50* (2006.01)
*G01N 33/92* (2006.01)
*C12Q 1/6883* (2018.01)

(52) U.S. Cl.
CPC ....... *G01N 33/6893* (2013.01); *C12Q 1/6883* (2013.01); *G01N 33/5076* (2013.01); *G01N 33/5091* (2013.01); *G01N 33/566* (2013.01); *G01N 33/92* (2013.01); *C12Q 2600/158* (2013.01); *G01N 2333/46* (2013.01); *G01N 2800/044* (2013.01); *G01N 2800/52* (2013.01)

(58) Field of Classification Search
CPC .......... G01N 33/6893; G01N 2333/46; G01N 2800/044; G01N 2800/52; C12Q 1/6883; C12Q 2600/158
See application file for complete search history.

(56) References Cited

U.S. PATENT DOCUMENTS

| 8,637,254 B2 | 1/2014 | Taylor et al. |
| 2012/0134998 A1 | 5/2012 | Hotamisligil et al. |
| 2013/0195899 A1 | 8/2013 | Ichim et al. |
| 2014/0065240 A1 | 3/2014 | Mitsialis et al. |

FOREIGN PATENT DOCUMENTS

WO    2017/194499 A1    11/2017

OTHER PUBLICATIONS

Ferrante, S.C. et al. Adipocyte-derived exosomal miRNAs: A novel mechanism for obesity-related disease. Pediatric Research, 2015, vol. 77(3), p. 447-454, epublished Dec. 2014.*
Momen-Heravi, F., et al. Current methods for the isolation of extracellular vesicles. Bio. Chem., 2013, 394(10):1253-1262.*
Vlassov, A.V., et al. Exosomes: Current knowledge of their composition, biological functions, and diagnostic and therapeutic potentials. Biochmica et Biophysica Acta, 2012, 1820:940-948.*
Witwer, K.W., et al. Standardization of sample collection, isolation and analysis methods in extracelluar vesicle research. Journal of Extracellular Vesicles, 2013, 2:20360, 25 pages.*
NHLBI Obesity Education Initiative, NIH Publication No. 00-4084, published Oct. 2013, p. 1-80.*
Ertunc, M.E. et al. Secretion of fatty acid binding protein aP2 from adipocytes through a nonclassical pathway in response to adipocyte lipase activity. J. Lipid Research, 2015, 56:423-434.*
Thoidis, G., et al., "Immunological analysis of GLUT4-enriched vesicles. Identification of novel proteins regulated by insulin and diabetes" J. Biol. Chem. (1993) 268(16):11691-6.
Anonymous, "FABP4/Ap2 Antibody (C-terminus, Magnetic Beads) LS-C171962" LSBio, retrieved from the Internet on Oct. 5, 2018: https://www.lsbio.com/antibodies/fabp4-antibody-ap2-antibody-c-terminus-magnetic-beads-ip-ls-c171962/179363.
Lee, J.E., et al., "Proteomic Analysis of Extracellular Vesicles Released by Adipocytes of Otsuka Long-Evans Tokushima Fatty (OLETF) Rats" Protein J. (2015) 34(3):220-35.
Ferrante, S., et al., "Adipocyte Exosomal miRNAs may Mediate the Effects of Obesity on Lung Disease" J. Invest. Med. (2013) 61(3):666-667.
Rome, S., "Are extracellular microRNAs involved in type 2 diabetes and related pathologies?" Clin. Biochem. (2013) 46(10-11):937-45.

(Continued)

*Primary Examiner* — Ruixiang Li
(74) *Attorney, Agent, or Firm* — Robert C. Netter, Jr.; Dann, Dorfman, Herrell & Skillman

(57) ABSTRACT

The invention relates to isolation of adipocyte-derived exosomes from a biological sample, as well as methods, compositions and kits for detecting an obesity-related disorder, for detecting risk of having an obesity-related disorder, for screening or identifying a therapy for an obesity-related disorder, for screening or identifying a therapeutic agent for an obesity-related disorder, and for treating or preventing an obesity-related disorder.

6 Claims, 6 Drawing Sheets

(56) References Cited

OTHER PUBLICATIONS

Karolina, D.S., et al., "Circulating miRNA profiles in patients with metabolic syndrome" J Clin. Endocrinol. Metab. (2012) 97(12):E2271-6.

Kranendonk, M.E., et al., "Extracellular vesicle markers in relation to obesity and metabolic complications in patients with manifest cardiovascular disease" Cardiovasc. Diabetol. (2014) 13:37.

Hubal, M.J., et al., "Circulating adipocyte-derived exosomal MicroRNAs associated with decreased insulin resistance after gastric bypass" Obesity (2017) 25(1):102-110.

Ferrante, S.C., et al., "Adipocyte-derived Exosomal miRNAs: A Novel Mechanism for Obesity-Related Disease" Pediatr. Res. (2015) 77(3): 447-454.

Deng, Z.B., et al., "Adipose Tissue Exosome-Like Vesicles Mediate Activation of Macrophage-Induced Insulin Resistance" Diabetes (2009) 58:2498-2505.

Camussi, G., et al., "Exosome/microvesicle-mediated epigenetic reprogramming of cells" Am. J. Cancer Res. (2011) 1(1):98-110.

Koeck, E.S., et al., "Adipocyte exosomes induce transforming growth factor beta pathway dysregulation in hepatocytes: a novel paradigm for obesity-related liver disease" J. Surg. Res. (2014) 192(2):268-75.

Ussar, S., et al., "Asc-1, PAT2 and P2RX5 are novel cell surface markers for white, beige and brown adipocytes" Sci. Transl. Med. (2014) 6(247):247ra103.

Khalyfa, A., et al., "Circulating Plasma Extracellular Microvesicle MicroRNA Cargo and Endothelial Dysfunction in Children with Obstructive Sleep Apnea" Am. J. Respir Crit. Care Med. (2016) 194(9):1116-1126.

Kishida, K., et al., "Visceral adiposity as a target for the management of the metabolic syndrome" Annals of Medicine (2012) 44: 233-241.

Zernecke, A. et al., "Delivery of MicroRNA-126 by Apoptotic Bodies Induces CXCL12-Dependent Vascular Protection" Science Signaling (2009) 2(100):ra81.

Xu, A., et al., "Adipocyte fatty acid-binding protein is a plasma biomarker closely associated with obesity and metabolic syndrome" Clin. Chem. (2006) 52(3):405-13.

Hubal, M.J., et al., "Circulating Adipocyte-Derived Exosomal MicroRNAs Associated with Decreased Insulin Resistance After Gastric Bypass" Obesity (2017) 25:102-110.

Herrera, B.M., et al., "Global microRNA expression profiles in insulin target tissues in a spontaneous rat model of type 2 diabetes" Diabetologia (2010) 53:1099-1109.

Davalos, A., et al., "miR-33a/b contribute to the regulation of fatty acid metabolism and insulin signaling" PNAS (2011) 108:9232-9237.

Higuchi, C., et al., "Identification of Circulating miR-101, miR-375 and miR-802 as Biomarkers for Type 2 Diabetes" Metab. Clin. Exper. (2015) 64:489-497.

Connolly, et al., "Characterisation of adipocyte-derived extracellular vesicles released pre- and post-adipogenesis" J. Extracell. Vesicles (2015) 4:29159.

* cited by examiner

ADIPOCYTE-DERIVED EXOSOMES, AND COMPOSITIONS, KITS, AND METHODS OF USING THE SAME FOR DETECTION AND SCREENING

RELATED APPLICATIONS

This application is a § 371 application of PCT/US2016/036880, filed Jun. 10, 2016, which claims the benefit of U.S. Provisional Patent Application Ser. No. 62/173,496, filed Jun. 10, 2015, and U.S. Provisional Patent Application Ser. No. 62/336,943, filed May 16, 2016, the disclosures of which are incorporated herein in their entirety by reference.

FIELD OF THE INVENTION

This application relates generally to the field of exosomes, and more particularly, to adipocyte-derived exosomes. This application also relates generally to the isolation of exosomes, such as adipocyte-derived exosomes, from biological samples including fluids, such as, for example, urine and blood. Exosomes are actively-shed endocytic vesicles that are capable of transporting functional mRNAs, microRNAs, and proteins between cells over large distances; exosomes therefore may contribute to mechanisms by which adipocytes (and adipose tissue) in obese individuals can induce dysfunction in other organ systems. See Kishida et al. (*Ann. Med.*, 2012, 44(3): 233-41, the entirety of which is incorporated by reference herein; Camussi et al. (*Am. J. Cancer Res.*, 2011, 1(1): 98-110, the entirety of which is incorporated by reference herein; and Zernecke et al. (*Sci. Signal*, 2009, 2(100): ra81), the entirety of which is incorporated by reference herein.

BACKGROUND INFORMATION

Adipose tissue is an active endocrine organ, which synthesizes and releases adipokines (such as leptin, resistin and adiponectin) that act as autocrine, paracrine and endocrine factors to modulate metabolism locally and at distant sites. See Sun et al. (*J. Clin. Invest.*, 2011, 121(6): 2094-101, the entirety of which is incorporated by reference herein). Ectopic adipose accumulation can significantly compromise insulin sensitivity by interfering with insulin signaling. See Shulman (*N. Engl. J. Med.*, 2014, 371(12): 1131-41, the entirety of which is incorporated by reference herein).

Exosomes are nanoparticle-sized endocytic vesicles that transport lipids, sugars, nucleic acids, and proteins between cells. See Camussi et al. and Zernecke et al., supra. Adipose exosomal signaling is largely determined by their microRNA content, which can control gene expression in target cells by inhibiting mRNA translation or enhancing mRNA degradation. See Karelis et al. (*J. Clin. Endocrinol. Metab.*, 2004, 89(6): 2569-75, the entirety of which is incorporated by reference herein); and Bartel (*Cell*, 2009, 136(2): 215-33, the entirety of which is incorporated by reference herein).

Insulin resistance in patients with obesity significantly contributes to the pathogenesis of chronic metabolic diseases such as Type II diabetes mellitus (T2DM). Adipose is a key modulator of systemic insulin resistance and metabolic dysregulation, exerting effects via mechanisms such as releasing pro-inflammatory cytokines into the circulation. See Sun et al. supra; Boden et al. (*Diabetes*, 2014, 63(9): 2977-83, the entirety of which is incorporated by reference herein); Kim et al. (*Clin. Invest.*, 2007, 117(9): 2621-37, the entirety of which is incorporated by reference herein); and Tilg et al. (*Nat. Rev. Immunol.*, 2006, 6(10): 772-83, the entirety of which is incorporated by reference herein). Central adiposity is strongly linked to the pathogenesis of obesity-related comorbidities like insulin resistance in peripheral tissues. See Marette et al. (*Rev. Endocr. Metab. Disord.*, 2014, 15(4): 299-305, the entirety of which is incorporated by reference herein); and Sam et al. (*Transl. Res.*, 2014, 164(4): 284-92, the entirety of which is incorporated by reference herein). However, large variations exist in an individual's response to obesity; some patients with high body mass index (BMI) can have normal glucose homeostasis, while others with normal BMI can have frank diabetes. See Gomez-Ambrosi et al. (Int. J. Obes. (Lond), 2012, 36(2): 286-94, the entirety of which is incorporated by reference herein). The volume of adipose tissue alone therefore does not portend systemic disease, and it is contemplated that adipose function must also play a critical role.

One potential mechanism linking adipose accumulation to overall glucose regulation is inter-organ signaling from adipose tissue via exosomes. Deng et al. (*Diabetes*, 2009. 58(11): 2498-505, the entirety of which is incorporated by reference herein) suggested that adipocyte-derived exosomes might affect insulin resistance, finding that obesity-related microRNAs targeted key biological pathways that impact insulin signaling using an animal model. Previous studies have described obesity-related differences in the microRNA content of exosomes derived from human obese visceral adipose tissue, as compared to those from lean subjects, and identified adipocyte-derived exosomal signaling as a mediator linking adiposity and insulin resistance in peripheral tissues. See Ferrante et al., supra; and Koeck et al. (*J. Surg. Res.*, 2014, 192(2): 268-75, the entirety of which is incorporated by reference herein). However, previous studies have relied upon isolating adipocyte-derived exosomes from adipose tissue, due to the absence of any technique for effectively isolating adipocyte-derived exosomes from other sources.

There is a strong epidemiological link between obesity and atherosclerosis (Bastien, M., et al., (*Prog Cardiovasc Dis*, 2014. 56(4): p. 369-81, the entirety of which is incorporated by reference herein); and Gupta, N., et al., (*Endocr Rev*, 2012. 33(1): p. 48-70, the entirety of which is incorporated by reference herein). Atherosclerosis, which is one of the hallmarks of cardiovascular disease, is characterized by macrophage cholesterol efflux impairment leading to intracellular accumulation of modified low-density lipoprotein (LDL) and subsequent formation of plaque-forming lipid-rich foam cells. Michael, D. R., et al. (*Cytokine*, 2013. 64(1): p. 357-61, the entirety of which is incorporated by reference herein); and Rohatgi, A., et al., (*N Engl J Med*, 2014. 371(25): p. 2383-93, the entirety of which is incorporated by reference herein). Macrophage cholesterol homeostasis is a delicate balance among influx, endogenous synthesis, esterification/hydrolysis and efflux. See Zhang, M., et al., (*Atherosclerosis*, 2014. 234(1): p. 54-64, the entirety of which is incorporated by reference herein). Large variations exist in individual responses to obesity. For example, some patients with high adiposity have normal cardiovascular health, while others with low adiposity have frank atherosclerosis. See Bradshaw, P. T., K. L. Monda, and J. Stevens. (*Obesity* (Silver Spring), 2013. 21(1): p. 203-9, the entirety of which is incorporated by reference herein). It is contemplated that adipose health or function, not adipose mass per se, is a determinant of obesity-related comorbidities. However, tools to assess adipose health/function in relation to the comorbidities are lacking.

SUMMARY OF THE INVENTION

The present disclosure relates to techniques for the isolation, quantification, and/or characterization of adipocyte-derived exosomes. In some embodiments of the invention, for example, adipocyte-derived exosomes may be isolated and/or quantified from the circulation and/or the urine, and additionally, their contents may subsequently be characterized. This facile isolation procedure has implications for the generation of convenient and rapid diagnostic tests, and for the development, testing, and monitoring of therapeutics. In some aspects, the subject from which the exosomes are isolated may be a subject in need of weight loss, or may be in need of a modification to their adipocyte-derived exosome microRNA profile. This exosome microRNA profile may include, for example, the presence or absence of particular microRNAs, and/or the abundance of particular microRNAs, including the relative abundance of a microRNA with respect to the abundance of one or more other microRNAs.

According to one embodiment, a process of the present invention involves isolating adipocyte-derived exosomes from a subject. A biological sample is obtained (from a subject) that contains adipocyte-derived exosomes, and the adipocyte-derived exosomes are specifically isolated from the sample using a binding agent which binds to at least one marker specific for adipocyte-derived exosomes. This marker may be, for example, selected from the group consisting of Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, N-acetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4).

In some embodiments, the process may involve using Fatty Acid Binding Protein 4 (FABP4) as a marker. Additionally, the biological sample obtained may be, but is not limited to, milk, blood, serum, plasma, ascites, cyst fluid, pleural fluid, peritoneal fluid, cerebral spinal fluid, tears, urine, saliva, sputum, or combinations thereof. In particular embodiments, the biological sample obtained is blood, serum, or urine.

In some embodiments, the process may involve using a binding agent such as an anti-FABP4 antibody, or an antigen-binding fragment thereof.

In some embodiments, the process may involve isolating the adipocyte-derived exosomes using magnetic beads. The isolated adipocyte-derived exosomes may be substantially free of other non-adipocyte-derived exosomes, or completely free of other non-adipocyte-derived exosomes, if desired.

The sample may be collected from a lean subject, an overweight subject, or an obese subject. In some embodiments, the sample may be collected from an obese subject prior to initiation of a weight-loss treatment, surgery, or regimen. Alternatively, the sample may be collected from an obese subject after initiation or completion of a weight-loss treatment, surgery, or regimen.

In a second aspect of the invention, a kit for isolating adipocyte-derived exosomes in a biological sample is provided. The kit may contain a binding agent which specifically binds to at least one marker specific for adipocyte-derived exosomes, a bioparticle for isolation of the adipocyte-derived exosomes, and instructions for performing the adipocyte-derived exosome isolation.

The kit may include at least one marker, as a control for example. The marker may be, but is not limited to, Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, N-acetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and/or frizzled-4 (Fzd4).

The bioparticle for isolation of the adipocyte-derived exosomes may comprise, for example, a magnetic bead or an agarose bead. In particular embodiments, the bioparticle is at least one magnetic bead selected from the group consisting of a sepharose magnetic bead, a streptavidin magnetic bead, a Protein A magnetic bead, a Protein G magnetic bead, a ferromagnetic bead, a magnetic nanosphere, a magnetic microsphere, and a polyvinyl alcohol magnetic particle (M-PVA Magnetic Bead)

In some embodiments, the kit provided for performing the process of isolating adipocyte-derived exosomes in a biological sample includes a binding agent that specifically binds to Fatty Acid Binding Protein 4 (FABP4), at least one magnetic bead, and instructions for performing the adipocyte-derived exosome isolation.

In a third aspect of the invention, a method of detecting an obesity-related disorder in a subject is provided. The method may involve, for example, obtaining a biological sample from a subject which contains adipocyte-derived exosomes, isolating adipocyte-derived exosomes from the biological sample using a binding agent which binds to at least one marker specific for adipocyte-derived exosomes, and detecting that the subject has an obesity-related disorder by a measurable change in a profile of the isolated adipocyte-derived exosomes from the subject. The measurable change may be relative to, for example, a profile of adipocyte-derived exosomes from one or more control subjects.

In a fourth aspect of the invention, a method of detecting an increased risk of a subject for having an obesity-related disorder is provided. The method may involve, for example, obtaining a biological sample from a subject which contains adipocyte-derived exosomes, isolating adipocyte-derived exosomes from the biological sample using a binding agent which binds to at least one marker specific for adipocyte-derived exosomes, and detecting the subject has an increased risk of having an obesity-related disorder by a measurable change in a profile of the isolated adipocyte-derived exosomes from the subject. The measurable change may be relative to, for example, a profile of adipocyte-derived exosomes from a control subject.

The detection methods of the present invention may further include applying the profile of the isolated adipocyte-derived exosomes from the subject against the profile of adipocyte-derived exosomes from one or more control subjects.

The detection methods of the present invention may further include diagnosing the subject as having an obesity-related disorder, or an increased risk of having an obesity-related disorder.

The detection methods may further include determining the profile of the isolated adipocyte-derived exosomes.

The detection methods may further include administering at least one therapeutic agent to the subject to treat the obesity-related disorder.

The detection methods may further include recommending to the subject, a therapy comprising a therapeutic regimen, a surgical intervention, a behavioral modification, or a combination thereof.

In a fifth aspect of the invention, a method for identifying a therapy for an obesity-related disorder in a subject is provided. The method involves obtaining a biological sample from the subject which contains adipocyte-derived exosomes, isolating adipocyte-derived exosomes from the biological sample using a binding agent which binds to at least one marker specific for adipocyte-derived exosomes, and detecting the subject has an obesity-related disorder, or has an increased risk of having an obesity-related disorder, by a measurable change in a profile of the isolated adipocyte-derived exosomes from the subject. The measurable change may be relative to, for example, a profile of adipocyte-derived exosomes from a control subject. Based on this detected measurable change, a therapy for the obesity-related disorder is then identified. The therapy may include, for example, a therapeutic regimen, a surgical intervention, a behavioral modification, or a combination thereof.

In particular embodiments, the surgical intervention may be bariatric surgery or bypass surgery.

The therapeutic regimen may include administering at least one therapeutic agent, a dietary intervention, exercise, or a combination thereof.

The method for identifying a therapy for an obesity-related disorder in a subject may further include determining the profile of the isolated adipocyte-derived exosomes from the subject.

The method for identifying a therapy for an obesity-related disorder in a subject may further include applying the profile of the isolated adipocyte-derived exosomes from the subject against the profile of adipocyte-derived exosomes from the control subject.

The method for identifying a therapy for an obesity-related disorder in a subject may further include administering the identified therapy to the subject.

The method for identifying a therapy for an obesity-related disorder in a subject may further include recommending the identified therapy to the subject.

In a sixth aspect of the invention, a method for identifying at least one therapeutic agent for an obesity-related disorder in a subject is provided. The method involves obtaining a biological sample from a subject which contains adipocyte-derived exosomes, isolating adipocyte-derived exosomes from the biological sample using a binding agent which binds to at least one marker specific for adipocyte-derived exosomes, detecting the subject has an obesity-related disorder, or an increased risk of having an obesity-related disorder, by a measurable change in a profile of the isolated adipocyte-derived exosomes from the subject relative to a profile of adipocyte-derived exosomes from a control subject, and identifying the at least one therapeutic agent for treatment or prevention of the obesity-related disorder.

The therapeutic agent identified includes a therapeutic agent for treatment or prevention of a glucose homeostasis disorder, an agent for treatment or prevention of a respiratory disorder, an agent for treatment or prevention of a cardiovascular disorder, an agent for treatment or prevention of a neoplastic disease, an agent for treatment or prevention of a gallbladder disease, an agent for treatment or prevention of arthritis, an agent for dyslipidemia, an agent for mental illness, an agent for pain syndromes, or a combination thereof.

At least one therapeutic agent for a glucose homeostasis disorder includes orlistat, lorcaserin, phentermine, liraglutide, insulin, amylin, leptin, glucagon, glucagon-like peptide (GLP-1), glucagon-like peptide (GLP-1) receptor agonist, a sulfonylurea, a biguanide, somatostatin, diazoxide, a sodium-glucose co-transporter 2 (SGLT-2) inhibitor, acarbose, miglitol, a dopamine agonist, a dipeptidyl peptidase 4 (DPP-4) inhibitor, a meglitinide, an α-glucosidase inhibitor, a thiazolidinedione, or a combination thereof.

At least one therapeutic agent for a cardiovascular disorder includes an aldosterone receptor antagonist, an angiotensin II receptor antagonist, an angiotensin converting enzyme inhibitor, a β-adrenergic receptor antagonist, a calcium channel blocker, an $\alpha_2$-adrenergic receptor agonist, an $\alpha_1$-adrenergic receptor antagonist, a vasodilator, a cardiac glycoside, a diuretic, an inotropic agent, a phosphodiesterase inhibitor, an antiarrhythmic agent, potassium, a proprotein convertase subtilisin kexin type 9 (PCSK9) inhibitor, a nitrate, warfarin, a cholesterol lowering agent, or a combination thereof. At least one therapeutic agent for a respiratory disorder includes a β-adrenergic receptor agonist, an antihistamine, a leukotriene modifier, a mast cell stabilizer, theophylline, an immunomodulator, an anticholinergic, and a corticosteroid, or a combination thereof.

The method for identifying at least one therapeutic agent for an obesity-related disorder in a subject may further include applying the profile of the isolated adipocyte-derived exosomes from the subject against the profile of adipocyte-derived exosomes from the control subject.

The method for identifying at least one therapeutic agent for an obesity-related disorder in a subject may further include determining the profile of the isolated adipocyte-derived exosomes from the subject.

The method for identifying at least one therapeutic agent for an obesity-related disorder in a subject may further include administering the at least one therapeutic agent to the subject.

The method for identifying at least one therapeutic agent for an obesity-related disorder in a subject may further comprise recommending the at least one therapeutic agent to the subject.

In a seventh aspect of the invention, a method of treating or preventing an obesity-related disorder in a subject is provided, which method may comprise obtaining a biological sample from a subject which contains adipocyte-derived exosomes, isolating adipocyte-derived exosomes from the biological sample using a binding agent which binds to at least one marker specific for adipocyte-derived exosomes, detecting the subject has an obesity-related disorder or an increased risk of having an obesity-related disorder by a measurable change in a profile of the isolated adipocyte-derived exosomes from the subject relative to a profile of adipocyte-derived exosomes from a control subject, and administering a therapy to the subject to treat or prevent the obesity-related disorder. The therapy may include, for example, a therapeutic regimen, surgical intervention, behavioral modification, or a combination thereof. The surgical intervention includes bariatric surgery or bypass surgery. The therapeutic regimen includes administering at least one therapeutic agent.

The obesity-related disorder may include, for example, a glucose homeostasis disorder, a respiratory disorder, a cardiovascular disorder, a neoplastic disease, gallbladder disease, arthritis, or a combination thereof.

The glucose homeostasis disorder may include, for example, diabetes, insulin resistance, glycosuria, hyperglycemia, hyperinsulinism, and/or hypoglycemia. Diabetes may be diabetes mellitus type I, diabetes mellitus type II and gestational diabetes.

The cardiovascular disorder may include, for example, atherosclerosis, coronary artery disease, stroke, peripheral artery disease, angina, myocardial infarction, hypertension, and hypertensive heart disease.

The respiratory disorder may include, for example, asthma, sleep apnea, obesity hypoventilation syndrome and chronic obstructive pulmonary disease.

The profile of the isolated adipocyte-derived exosomes may be, for example, a microRNA expression profile, a protein expression profile, an mRNA expression profile, a lipid profile, a sugar profile, and/or a nucleic acid profile.

In some embodiments, the profile of the isolated adipocyte-derived exosomes from the subject, and the profile of the adipocyte-derived exosomes from the control subject, are each an microRNA expression profile that includes an expression level of at least one microRNA. The expression level of the at least one microRNA from the subject may be higher than the corresponding expression level of the at least one microRNA from the control subject.

In other embodiments, the profile of the isolated adipocyte-derived exosomes from the subject, and the profile of the adipocyte-derived exosomes from the control subject, are each an microRNA expression profile that includes an expression level of at least one microRNA, and the expression level of the at least one microRNA from the subject may be lower than the corresponding expression level of the at least one microRNA from the control subject.

The microRNA expression profile may include an expression level of at least one microRNA, such as miR-33a, miR-10b, miR-20a, miR-374b, miR-504, miR-101-1, let-7a-5p and miR-16-5p.

The subject may be a mammalian subject such as a human.

The biological sample may or may not include adipose tissue, and in some embodiments, adipose tissue is excluded from the biological sample. In some embodiments, the biological sample may include, for example, milk, blood, serum, plasma, ascites, cyst fluid, pleural fluid, peritoneal fluid, cerebral spinal fluid, tears, urine, saliva, sputum, or combinations thereof. In some embodiments, the biological sample is blood, serum, or urine.

The biological sample may be obtained from a lean subject or an obese subject. In some embodiments, the biological sample may be obtained from an obese mammalian subject prior to initiation of a weight-loss treatment, surgery, or regimen. Alternatively, the biological sample may be obtained from an obese mammalian subject after initiation or completion of a weight-loss treatment, surgery, or regimen.

The at least one marker includes, but is not limited to, Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, N-acetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and/or frizzled-4 (Fzd4). In a particular embodiment, the marker is Fatty Acid Binding Protein 4 (FABP4).

In a particular embodiment, an anti-FABP4 antibody, or antigen-binding fragment thereof, is the binding agent.

In another embodiment, the methods of the invention include use of magnetic beads to isolate adipocyte-derived exosomes.

The binding agent and the at least one marker specific for adipocyte-derived exosomes form a complex.

In one particular aspect of the invention, a method for isolating FABP4+ adipocyte-derived exosomes from a human subject is provided. The method involves obtaining a biological sample from the human subject which contains FABP4+ adipocyte-derived exosomes, and isolating FABP4+ adipocyte-derived exosomes from the biological sample using a FABP4+ antibody. The biological sample may be, for example, blood, serum or urine, and the FABP4+ adipocyte-derived exosomes are isolated using magnetic beads.

In another aspect of the invention, a method of detecting an obesity-related disorder in a human subject is provided. The method involves obtaining a biological sample from the human subject which contains FABP4+ adipocyte-derived exosomes, isolating FABP4+ adipocyte-derived exosomes from the biological sample using a FABP4+ antibody, and detecting the human subject has the obesity-related disorder by a measurable change in a microRNA expression profile of the FABP4+ isolated adipocyte-derived exosomes from the human subject relative to a corresponding microRNA expression profile of FABP4+ adipocyte-derived exosomes from a control human subject. The biological sample is blood, serum or urine, and the FABP4+ adipocyte-derived exosomes are isolated using magnetic beads. An expression level of at least one microRNA in the microRNA expression profile of isolated of FABP4+ adipocyte-derived exosomes from the human subject is higher relative to an expression level of at least one microRNA in the corresponding microRNA expression profile of FABP4+ adipocyte-derived exosomes from the control human subject.

In yet another aspect of the invention, a method of detecting susceptibility of a subject to an obesity-related disorder is provided. The method involves obtaining a biological sample from a subject which contains FABP4+ adipocyte-derived exosomes, isolating FABP4+ adipocyte-derived exosomes from the biological sample using a FABP4+ antibody, and detecting the human subject has an increased risk of having an obesity-related disorder by a measurable change in a microRNA expression profile of the FABP4+ isolated adipocyte-derived exosomes from the human subject relative to a corresponding microRNA expression profile of FABP4+ adipocyte-derived exosomes from a control human subject. The biological sample may be, for example, blood, serum or urine, and the FABP4+ adipocyte-derived exosomes may be isolated using magnetic beads. An expression level of at least one microRNA in the microRNA expression profile of isolated of FABP4+ adipocyte-derived exosomes from the human subject is higher relative to an expression level of at least one microRNA in the corresponding microRNA expression profile of FABP4+ adipocyte-derived exosomes from the control human subject.

In still another aspect of the invention, a method for identifying a therapy for an obesity-related disorder in a human subject is provided. The method involves obtaining a biological sample from the human subject which contains FABP4+ adipocyte-derived exosomes, isolating FABP4+ adipocyte-derived exosomes from the biological sample using a FABP4+ antibody, detecting the human subject has the obesity-related disorder or an increased risk of having an obesity-related disorder, by a measurable change in a microRNA expression profile of the FABP4+ isolated adipocyte-derived exosomes from the human subject relative to a corresponding microRNA expression profile of FABP4+ adipocyte-derived exosomes from a control human subject, and identifying the therapy for the obesity-related disorder. The biological sample may be, for example, blood, serum or urine, and the FABP4+ adipocyte-derived exosomes may be isolated using magnetic beads. An expression level of at least one microRNA in the microRNA expression profile of isolated of FABP4+ adipocyte-derived exosomes from the human subject is higher relative to an expression level of at least one microRNA in the corresponding microRNA expression profile of FABP4+ adipocyte-derived exosomes from the control human subject.

In a particular aspect of the invention, a method of identifying at least one therapeutic agent for an obesity-related disorder in a human subject is provided. The method involves obtaining a biological sample from the human subject which contains FABP4+ adipocyte-derived exosomes, isolating FABP4+ adipocyte-derived exosomes from the biological sample using a FABP4+ antibody, detecting the human subject has the obesity-related disorder or an increased risk of having an obesity-related disorder, by a measurable change in a microRNA expression profile of the FABP4+ isolated adipocyte-derived exosomes from the human subject relative to a corresponding microRNA expression profile of FABP4+ adipocyte-derived exosomes from a control human subject, and identifying the at least one therapeutic agent for the obesity-related disorder. The biological sample may be, for example, blood, serum or urine, and the FABP4+ adipocyte-derived exosomes may be isolated using magnetic beads. An expression level of at least one microRNA in the microRNA expression profile of isolated of FABP4+ adipocyte-derived exosomes from the human subject is higher relative an expression level of at least one microRNA in the corresponding microRNA expression profile of FABP4+ adipocyte-derived exosomes from the control human subject.

In still another particular aspect of the invention, a method for treating or preventing an obesity-related disorder in a human subject is provided. The method involves obtaining a biological sample from the human subject which contains FABP4+ adipocyte-derived exosomes, isolating FABP4+ adipocyte-derived exosomes from the biological sample using a FABP4+ antibody, detecting the human subject has the obesity-related disorder or an increased risk of having an obesity-related disorder, by a measurable change in a microRNA expression profile of the isolated FABP4+ adipocyte-derived exosomes from the human subject relative to a corresponding microRNA expression profile of FABP4+ adipocyte-derived exosomes from a control human subject, and administering a therapy to treat or prevent the obesity-related disorder. The biological sample may be, for example, blood, serum or urine, and the FABP4+ adipocyte-derived exosomes may be isolated using magnetic beads. An expression level of at least one microRNA in the microRNA expression profile of isolated of FABP4+ adipocyte-derived exosomes from the human subject is higher relative to an expression level of at least one microRNA in the corresponding microRNA expression profile of FABP4+ adipocyte-derived exosomes from the control human subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A) Fold changes (qRT-PCR) are presented comparing mock mimic transfection to that for miR33a and miR374b expression. FIG. 5B) ABCA1, 27-hydroxylase, PPARγ, and LXRα proteins were assayed via Western blot and show similar downregulation.

DETAILED DESCRIPTION OF THE INVENTION

Figure 1:
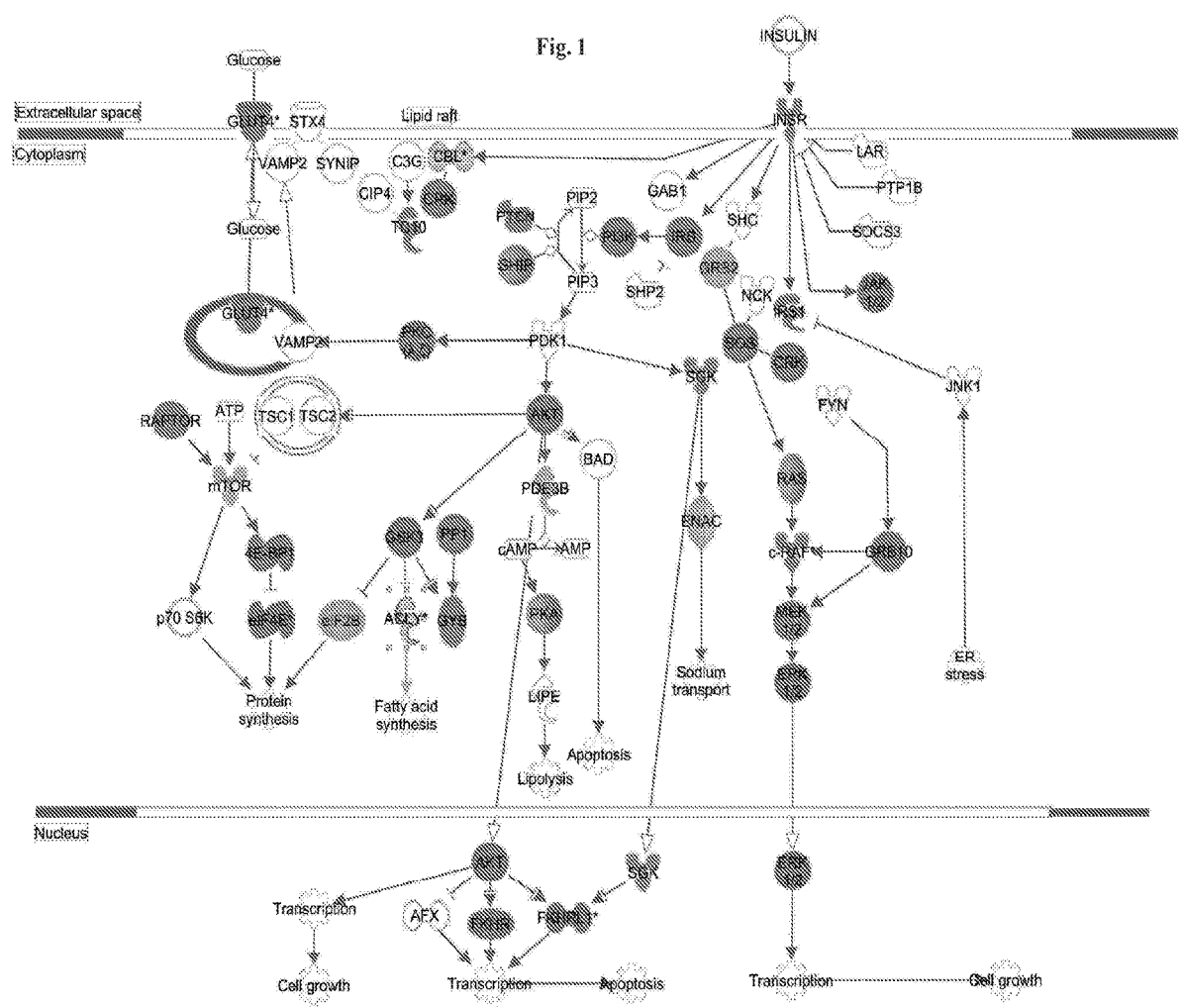
FIG. 1 depicts Insulin Receptor Signaling Pathway Targeted by Surgery-Responsive microRNAs. The canonical pathway for Insulin Receptor Signaling was highly ranked as a target for surgery-responsive microRNAs. Green color indicates predicted downregulation of target transcripts by differentially expressed microRNAs (i.e. upregulated microRNAs that inhibit mRNA target production), and red color indicates predicted upregulation of mRNA targets. Specific fold changes and microRNA-mRNA pairings are detailed in Table 1.

The details of embodiments of the presently disclosed subject matter are set forth in the accompanying description below. Other features, objects, and advantages of the presently disclosed subject matter will be apparent from the specification, figures, and claims. All publications, patent applications, patents, and other references noted herein are incorporated by reference in their entirety.

As endocytic vesicles capable of transporting functional mRNAs, microRNAs, and proteins between cells over large distances, exosomes are a logical putative contributor to mechanisms by which adipocytes can influence other organ systems, such as in cardiovascular disease and metabolic syndrome (K. Kishida, T. Funahashi, Y. Matsuzawa, I. Shimomura, Visceral adiposity as a target for the management of the metabolic syndrome. *Ann Med* 44, 233-241 (2012)). Exosomes are actively shed endocytic vesicles that contain and transport functional mRNAs, microRNAs, and proteins between cells (G. Camussi et al., Exosome/microvesicle-mediated epigenetic reprogramming of cells. *Am J. Cancer Res* 1, 98-110 (2011); and A. Zernecke et al., Delivery of microRNA-126 by apoptotic bodies induces CXCL12-dependent vascular protection. *Sci Signal* 2, ra81 (2009)).

In obese individuals, adipocyte-derived exosomes such as adipocyte-derived exosomes (FABP4+) were understood to contribute to the development of insulin resistance via activation of adipose-resident macrophages and secretion of pro-inflammatory cytokines that can result in insulin resistance (Z. B. Deng et al., "Adipose tissue exosome-like vesicles mediate activation of macrophage-induced insulin resistance," *Diabetes* 58, 2498-2505 (2009); and S. C. Ferrante et al., Adipocyte-derived exosomal microRNAs: a novel mechanism for obesity-related disease. *Pediatr Res*, (2015)).

Obesity-related differences in the microRNA content of exosomes derived from human obese visceral adipose tissue as compared to those from lean subjects were described by Ferrante, S. C., et al., "Adipocyte-derived exosomal microRNAs: a novel mechanism for obesity-related disease," *Pediatr Res*, 2015. 77(3): p. 447-54). Adipocyte-derived exosomal signaling was identified as a mediator linking adiposity and insulin resistance in peripheral tissues. Ferrante, S. C. et al., "Adipocyte-derived exosomal microRNAs: a novel mechanism for obesity-related disease," *Pediatr Res*, 2015. 77(3): p. 447-54), and Koeck, E. S., et al., "Adipocyte exosomes induce transforming growth factor beta pathway dysregulation in hepatocytes: a novel paradigm for obesity-related liver disease," *J Surg Res*, 2014. 192(2): p. 268-75. While these previous experiments showed the chronic effects of obesity on adipocyte-derived exosomal microRNA contents, the ability of significant weight loss to reverse these changes and the potential for cardiometabolic health gains could not be determined. Although there was evidence that bariatric surgery led to weight loss, improved glucose regulation, and improved cardiometabolic health (Schauer, P. R., D. L. Bhatt, and S. R. Kashyap, "Bariatric surgery versus intensive medical therapy for diabetes," *N Engl J Med*, 2014. 371(7): p. 682); the mechanisms by which surgery produces these effects, and their interdependence, were unclear.

Surprisingly, adipocyte-derived exosomes and their functional mRNAs, microRNAs and proteins were found to be the direct link between obesity and its related diseases. As described herein, the novel techniques of the invention isolate, quantify, and characterize adipocyte-derived exosomes in the circulation and in urine. For instance, the exosomal content analyses show abundant microRNAs and distinct differences between obese and lean individuals. Further, serum samples before and after weight-loss surgery show normalization of obese adipocyte-derived exosomes' microRNA content toward a lean expression signature.

The adipocyte-derived exosomes are obtained from a biological sample from a subject. The subject may be a mammalian subject, including but not limited to, a human subject. The subject may be a lean subject, or an obese subject. The subject may be a lean subject or an obese subject before, during or after therapy.

As used herein, the terms "a," "an," "any," and "the" include both singular and plural forms. For example, reference to "a binding agent" includes a plurality of such binding agent and reference to "the binding agent" includes reference to one or more binding agent known to those skilled in the art.

The term "or" means "and/or" unless stated otherwise.

The term "comprise," "comprises," "comprising" "include," "includes," and "including" are interchangeable and not intended to be limiting.

It is to be further understood that where descriptions of various embodiments use the term "comprising," those skilled in the art would understand that the present disclosure also contemplates such embodiments alternatively described using the language "consisting essentially of" or "consisting of."

The term "antibody" includes, but is not limited to, polyclonal antibodies, multiclonal antibodies, monoclonal antibodies, chimeric antibodies, humanized and primatized antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof; antibody fragments such as Fab fragments, F(ab') fragments, single-chain FvFcs, single-chain Fvs; and derivatives thereof including Fc fusions and other modifications, and any other immunologically active molecule so long as they exhibit the desired biological activity (i.e., antigen association or binding). Moreover, the term further includes all classes of antibodies (i.e. IgA, IgD, IgE, IgG, and IgM) and all isotypes (i.e., IgG1, IgG2, IgG3, IgG4, IgA1, and IgA2), as well as variations thereof unless otherwise dictated by context.

The term "nucleic acid" includes DNA molecules and RNA molecules and artificial variants thereof (e.g., peptide nucleic acids), whether single-stranded or double-stranded. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector.

The term "measurable" or "measurably" means capable of being detected, detectable or discernible, and may represent a noticeable, observable, perceivable or visible difference.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, kits and compositions, the exemplary methods, devices and materials are described herein.

The methods, compositions and kits of the present invention can be used in an outpatient clinic, inpatient environment, or laboratory. The isolation method, detection method, compositions, and kits described herein are useful to identify, diagnose, and prognose subjects that should be followed or treated for an obesity-related disorder.

Any of the marker(s) and/or binding agent(s) described herein can be labeled by incorporating a detectable label measurable by spectroscopic, photochemical, biochemical, immunochemical, or chemical means. For example, such labels can comprise radioactive substances (e.g., $^{32}P$, $^{35}S$, $^{3}H$, $^{125}I$), fluorescent dyes (e.g., 5-bromodesoxyuridin, fluorescein, acetylaminofluorene, digoxigenin), biotin, nanoparticles, and the like.

A control subject may be a lean or an obese subject. The control subject may also be an obese or a lean subject prior to, during, or after therapy. Obese human subjects, in some aspects, may be defined as having a BMI≥98th percentile and lean human subjects as having a BMI≤13th percentile for age and sex. The control subject may be a group of subjects or individuals who are predicted to be representative of the general population having a particular genotype or expression profile. A control subject can include an individual who has not, or individuals who have not, demonstrated an obesity-related disorder and can include individual(s) whose family line does not or has not demonstrated any obesity-related disorder(s).

A "subject" includes an individual (e.g., a mammalian subject or human) whose gene expression profile, microRNA expression profile, mRNA expression profile, protein expression profile, lipid profile, sugar profile, or response to treatment for an obesity-related disease state, is to be determined or has been determined. The subject may be an obese or lean subject, preferably, an obese human subject or a lean human subject. The mammalian subject may include, but is not limited to, a subject suffering from an obesity-related disorder, a subject at risk for an obesity-related disorder, an obese subject prior to initiation of a weight-loss treatment, surgery or regimen, or an obese subject after initiation or completion of a weight-loss treatment, surgery, or regimen.

An obesity-related disorder or disease may include, but is not limited to, a glucose homeostasis disorder, a respiratory disorder, a cardiovascular disorder, a neoplastic disease, gallbladder disease, arthritis, dyslipidemia, a mental disorder, and a pain syndrome.

A glucose homeostasis disorder may include, but is not limited to, diabetes, insulin resistance, glycosuria, hyperglycemia, hyperinsulinism, and hypoglycemia. The diabetes may be diabetes mellitus type I, diabetes mellitus type II, or gestational diabetes.

A respiratory disorder may include, but is not limited to, asthma, sleep apnea, obesity hypoventilation syndrome, and chronic obstructive pulmonary disease.

A cardiovascular disorder may include, but is not limited to, atherosclerosis, coronary artery disease, stroke, peripheral artery disease, angina, myocardial infarction, hypertensive heart disease, and hypertension.

A neoplastic disease may or may not be malignant. In some embodiments, the neoplastic diseases may be solid or non-solid cancers. In other embodiments, the cancers may be refractory or relapses. The cancer may include, but is not limited to, leukemia, including acute myeloid leukemia (AML), chronic myeloid leukemia (CML), chronic myeloid leukemia blast crisis, myelodysplasia, and myeloproliferative syndrome; lymphoma, including Hodgkin's and non-Hodgkin's lymphoma; subcutaneous adenocarcinoma; ovarian teratocarcinoma; liver cancer; breast cancer; bone cancer; gastric or colon cancer; melanoma; lung cancer; pancreatic, non-small cell lung cancer and prostate cancer.

A gallbadder disease and gallstones may include, but is not limited to, gallstones, acute or chronic cholecystitis, choledocholithiasis, biliary dyskinesia, sclerosing cholangitis, gallbladder cancer, gallbladder polyps.

Arthritis may include, but is not limited to, osteoarthritis, rheumatoid arthritis, juvenile arthritis, psoriatic arthritis, and gout.

Dyslipidemia involves high levels of cholesterol and/or triglycerides in the blood, and includes, but is not limited to, hyperlipoproteinemia (hyperlipidemia) and hypertriglyeridemia.

A mental disorder may include, but is not limited to, depression and anxiety.

A pain syndrome may include, but is not limited to, arthritis (such as osteoarthritis or rheumatoid arthritis), chronic pain syndrome, fibromyalgia, and back pain.

A therapeutic regimen may include, but is not limited to, medication, procedures, and lifestyle changes. For example a therapeutic regimen may include administration of one or more agents (such as a therapeutic agent, a biologic, a dietary supplement, and/or herbal supplement), or a combination thereof. The therapeutic regimen may include administration of one or more therapeutic agent, a dietary intervention, exercise, or a combination thereof. The therapeutic regimen may also include a dosage or administration protocol such as a dosing regimen comprising from 1 to 5, or 2 to 3, doses administered per day, per week, or per month. In additional embodiments, dosages may be administered 3 times/week, 4 times/week, 5 times/week, only on weekdays, only in concert with other treatment regimens, on consecutive days, or in any appropriate dosage regimen depending on clinical and patient-specific factors. A dosage and administration protocol may include repeated dosing therapy over a course of several days or even one or more weeks or years. An effective treatment regime may also involve prophylactic dosage administered on a day or multi-dose per day basis lasting over the course of days, weeks, months or even years. An effective dose or multi-dose treatment regimen for the obesity-related disorder or disease may be selected to approximate a minimal dosing regimen that is necessary and sufficient to substantially prevent or alleviate the symptoms of the obesity-related disorder or disease. The amount, timing and mode of delivery of medication or procedures may be routinely adjusted on an individual basis, depending on such factors as weight, age, gender, and condition of the individual, whether the administration is prophylactic or therapeutic, and on the basis of other factors known to effect drug delivery, absorption, pharmacokinetics, including half-life, and efficacy.

A therapeutic agent may include but is not limited to an agent for treatment or prevention of a glucose homeostasis disorder, an agent for treatment or prevention of a respiratory disorder, an agent for treatment or prevention of a cardiovascular disorder, an agent for treatment or prevention of a neoplastic disease, an agent for treatment or prevention of a gallbladder disease, an agent for arthritis, an agent for dyslipidemia, an agent for a mental disorder (such as depression and/or anxiety), and an agent for a pain syndrome.

An agent for treatment or prevention of a glucose homeostasis disorder may include, but is not limited to, orlistat, lorcaserin, phentermine, liraglutide, insulin, amylin, leptin, glucagon, glucagon-like peptide (GLP-1), glucagon-like peptide (GLP-1) receptor agonist, a sulfonylurea (such as glyburide, glipizide, gliclazide, glimepiride, tolbutamide, acetohexamide, tolazamide, and chlorpropamide), a biguanide (such as metformin and phenformin), somatostatin, diazoxide, a sodium-glucose co-transporter 2 (SGLT-2)

inhibitor (such as empagliflozin, canagliflozin, dapagliflozin, and ipragliflozin), acarbose, miglitol, a dopamine agonist (such as bromocriptine), a dipeptidyl peptidase 4 (DPP-4) inhibitor (such as sitagliptin and saxagliptin), a meglitinide (such as repaglinide, natelginide, and mitiglinide), an α-glucosidase inhibitor (such as acarbose), and a thiazolidinedione (such as ciglitazone and pioglitazone).

An agent for a cardiovascular disorder may include, but is not limited to, an aldosterone receptor antagonist (such as spironolactone and eplerenone), an angiotensin II receptor antagonist (such as losartan, valsartan, irbesartan, and candesartan), an angiotensin converting enzyme inhibitor (such as benazepril, captopril, enalapril, fosinopril, lisinopril, perindopril, quinapril, trandopril, and ramipril), a β-adrenergic receptor antagonist (such as timolol, metoprolol, atenolol, and propanolol), a calcium channel blocker (such as verapamil, diltiazem, nicardipine, nifedipine, isradipine, amlodipine, felodipine, nimodipine, and bepridil), an $\alpha_2$-adrenergic receptor agonist (such as clonidine, guanabenz, and guanifacine), an $\alpha_1$-adrenergic receptor antagonist (such as prazosin, terazosin, and doxazosin), a vasodilator (such as hydralazine, minoxidil, sodium nitroprusside, and diazoxide), a cardiac glycoside (such as digoxin and digitoxin), a diuretic (such as acetazolamide, dichlorphenamide, methazolamide, glycerin, isosorbide, mannitol, urea, furosemide, bumetanide, ethacrynic acid, torsemide, hydrochlorothiazide, amiloride, triamterene, and spironolactone), an inotropic agent (such as dopamine and dobutamine), a phosphodiesterase inhibitor (such as amrinone, milrinone, dipyridamole, and vesnarinone), an antiarrhythmic agent (such as lidocaine, phenytoin, mexiletine, tocainide, procainamide, quinidine, diopyramide, moricizine, propafenone, flecainide, propranolol, sotalol, bretylium, amiodarone, magnesium, verapamil, diltiazem, digoxin, digitoxin, and adenosine), potassium, a proprotein convertase subtilisin kexin type 9 (PCSK9) inhibitor (such as alirocumab and evolocumab), a nitrate, warfarin, and a cholesterol lowering agent (such as simvastatin, nicotinic acid, cholestyramine, colestipol, probucol, clofibrate, gemfibrozil, fenofibrate, and ciprofibrate).

An agent for a respiratory disorder may include, but is not limited to a β-adrenergic receptor agonist (such as albuterol, formoterol, arformoterol, indacaterol, levalbuterol, metaproterenol, salmeterol, and terbutaline), an antihistamine (such as montelukast, zafirlukast, and zileuton), a leukotriene modifier (such as cromolyn sodium), a mast cell stabilizer (such as mometasone and nedocromil), theophylline, an immunomodulator (such as a omalizumab, lumiliximab, soluble IL-4 receptor, aerovant, mepolizumab, reslizumab, lebrikizumab, cyclosporine, tacrolimus, and daclizumab), an anticholinergic (such as aclidinium, tiotropium, and ipratropium), and a corticosteroid (such as epinephrine, fluticasone, and budesonide). In addition, treatment of a respiratory disorder may include use of a therapeutic device including, but is not limited to, a positive breathing device and a dental device.

An agent for dyslipidemia, may include, but is not limited to, bile acid binders (such as cholestyramine, colestipol, and colesevelam), fibrates (such as fenofibrate and gemfibrozil), niacin, cholesterol absorption inhibitors (such as ezetimibe), omega-3 fatty acid supplements, and statins (such as atorvastatin, fluvastatin, lovastatin, pravastatin, rosuvastatin, simvastatin, and pitavastatin).

An agent for a mental disorder may include, but is not limited to, an antidepressant (such as citralopram, fluvoxamine, escitalopram, paroxetine, sertraline, fluoxetine, ariprazole, doxepin, clomipramine, bupropion, amoxapine, nortriptylline, vortioxetine, duloxetine, trazodone, venlafaxine, desvenlafaxine, selegiline, amitryptylline, and levomilnacipran) and an anxiolytic (such as alprazolam, bromoazepam, chlordiazepoxide, clonazepam, diazepam, flurazepam, lorazepam, oxazepam, temazepam, triazolam, meprobamate, carisoprodol, lorbamate, citralopram, fluvoxamine, escitalopram, paroxetine, sertraline, fluoxetine, venlafaxine, desvenlafaxine, milnacipran, levomilnacipran, duloxetine, and sibutramine).

An agent for pain syndromes may include, but is not limited to, a non-steroidal anti-inflammatory drug (including diclofenac, ibuprofen, naproxen, aspirin, celecoxib, ketoprofen, piroxicam and sulindac), acetaminophen, capsaicin, a narcotic pain reliever (including opioid), a disease-modifying anti-rheumatic drug (including methotrexate, hydroxychloroquine, sulfasalazine, and leflunomide), a biologic (including abatacept, adalimumab, anakinra, certolizumab, pegol, etanercept, golimumab, infliximab, rituximab, tocilizumab, and tofactinib), a corticosteroid, hyaluronic acid, an antidepressant (including duloxetine, amitryptylline, desipramine, imipramine, and nortriptylline), an anti-gout agent (including steroids, NSAIDs, allopurinol, febuxostat, and probenecid), an agent for fibromyalgia (including duloxetine, pregabalin, and savella), and an agent for back pain (including NSAIDs; acetaminophen; an opioid such as oxycodone, codeine, morphine, and hydrocodone; a muscle relaxant such as flexeril, baclofen, metaloxalone, and carisoprodol; a benzodiazepine such as diazepam, flurazepam, triazolom, clonazepam, temazepam, and lorazepam, a non-benzodiazepine such as zolpidem, eszopiclone, and zaleplon, an anticonvulsant such as tiagabine, carbatrol, neurotonin, and topiramate, and an antidepressant such as nortryptylline, trazodone, amitryptylline, nefazodone, and duloxetine).

A biologic may include, but is not limited to, a vaccine, an allergenic, gene therapy, tissues, and recombinant therapeutic proteins. The biologic may be composed of sugars, proteins, or nucleic acids or complex combinations of these substances, or may be living entities such as cells and tissues. The biologic may be isolated from a variety of natural sources such as human, animal, or microorganism. Alternatively, the biologic may be produced by biotechnology methods and/or other known technologies in the field. The gene therapy may include gene silencing which includes, but is not limited to, use of a naked DNA plasmid, RNA interference (RNAi) (such as siRNA, ssRNA, and shRNA), an antisense oligonucleotide, and a ribozyme. For example, the biologic may be an antisense oligonucleotide that binds to an mRNA or microRNA described herein and as exemplified in Table 1, Table 2 and Table 3, or a ribozyme, antisense oligonucleotide, or RNAi that targets mRNA molecules involved in an obesity-related disorder described herein such as asthma, diabetes, or atherosclerosis. Other examples of a biologic include, but are not limited to, a peptidomimetic (such as peptides that mimic the EGFA domain of the LDLR that binds to PCSK9), an antibody (such as a monoclonal antibody that binds to and inhibits PCSK9), and a DNA mimic (such as an aptamer).

Surgical interventions may include, but are not limited to, bariatric surgery and bypass surgery. Bariatric surgery may be predominantly-malabsorptive procedures such as, for example biliopancreatic diversion, jejunoileal bypass, and endoluminal sleeve, predominantly-restrictive procedures such as, for example vertical banded gastroplasty, adjustable gastric band, sleeve gastrectomy, intragastric balloon and gastric plication, or mixed procedures such as, for example gastric bypass surgery, sleeve gastrectomy with duodenal switch and implantable gastric stimulation.

Behavioral modifications may include, but are not limited to, changes in diet, physical activity, monitoring stress, counseling, and support groups.

A biological sample refers to a sample obtained from a subject wherein the sample comprises cells, or can be cell free. The biological sample may include, but is not limited to, lood, sputum, saliva, tissue, stool, urine, serum cerebrospinal, cells, secretions or the like. Where the sample is a tissue, the tissue sample can be obtained by biopsy. The biological sample can also be obtained by a minimally invasive method, such as a swab, or a non-invasive sampling method, such as a urine sample can be obtained and used in the methods of the disclosure. The swab, for example, can be obtained from any part of the body such as the mouth.

In some embodiments the biological sample is a biological fluid. In certain embodiments, the biological sample includes, but is not limited to, milk, blood, serum, plasma, ascites, cyst fluid, pleural fluid, peritoneal fluid, cerebrospinal fluid, tears, urine, saliva, sputum, or combinations thereof. Preferably, the biological sample is blood, serum, or urine.

One embodiment involves the measurement of at least one marker specific to an adipocyte-derived exosome, with the selectivity and sensitivity required for managing and diagnosing subjects that have or may have a predisposition to an obesity-related disease or disorder.

In one aspect of the disclosure, expression levels of microRNA, mRNA, polynucleotides, proteins or fragments thereof, are used in the detection or determination of an obesity-related disorder or a predisposition to an obesity-related disorder. Such analysis of expression level is referred to as an expression profile. Alternatively, a lipid profile, sugar profile, or nucleic acid profile may also be used in the detection or determination of an obesity-related disorder or a predisposition to an obesity-related disorder.

In some embodiments, the adipocyte-derived exosomes are isolated from other components in the biological sample using a binding agent which binds to a marker on the surface of adipocyte-derived exosomes. In certain embodiments, the marker is selectively expressed, or selectively over-expressed, on adipocyte-derived exosomes so as to allow the selective or exclusive isolation of adipocyte-derived exosomes from non-adipocyte-derived exosomes. In some embodiments, the isolated exosomes are substantially all adipocyte-derived exosomes. In other embodiments, at least 80%, at least 90%, at least 95%, at least 98%, or at least 99% of the isolated exosomes are adipocyte-derived exosomes.

In some embodiments, the binding agent binds to at least one marker including, but not limited to, Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, N-acetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4). Such markers are described, for instance, in Ussar, S. et al., Sci. Transl. Med., 6(24): 247ra103 (2014 Jul. 30), doi: 10.1126/scitranslmed.3008490; the entirety of which is incorporated by reference herein.

In yet further embodiments, the binding agent may be, for example, an antibody or an antigen-binding fragment thereof, an aptamer, or a fusion protein containing a binding moiety to at least one of the markers described herein, including, but not limited to, an FABP4 binding moiety or a binding moiety of any one of the markers described herein. The binding agent may be used in conjunction with other components to facilitate isolation of exosomes, such as a bioparticle or by utilizing avidin/streptavidin interactions.

The bioparticle may include, but is not limited to, a magnetic bead or an agarose bead. The magnetic bead may include but is not limited to, a sepharose magnetic bead, a streptavidin magnetic bead, Protein A magnetic bead, Protein G magnetic bead, a ferromagnetic bead, a magnetic nanosphere, a magnetic microsphere, and a polyvinyl alcohol magnetic particle (M-PVA Magnetic Bead). For example, the binding agent may be conjugated directly or indirectly to the bioparticle. Where magnetic beads are used, bound exosomes may then be collected using a magnet. The isolated, bead-bound exosomes may then be re-suspended in an appropriate buffer.

Where the binding agent is an antibody, it may be, for example, a human antibody, a mouse antibody, a rat antibody, a domestic fowl antibody, a rabbit antibody or a goat antibody. It may also be a polyclonal or monoclonal antibody, or a variant thereof (such as an $F(ab')_2$, Fab', Fab or Fv fragment). The antibody may also be chimeric, humanized, or completely human.

Method for Isolating Adipocyte-Derived Exosomes

In one aspect of the invention, a method of isolating adipocyte-derived exosomes is provided, comprising:
  obtaining a biological sample from a subject which contains adipocyte-derived exosomes; and
  isolating the adipocyte-derived exosomes from the biological sample using a binding agent which binds to at least one marker specific for adipocyte-derived exosomes.

Exosomes may be isolated from freshly collected samples, or from samples that have been stored frozen or refrigerated. Biological samples may be clarified before exosome isolation, using, for example, a centrifugation, ultracentrifugation, filtration or ultrafiltration technique.

The exosome isolation procedure may also comprise additional steps, such as, for example, a density gradient purification step, an ultracentrifugation step, a filtration step, a sample concentration step, a dialysis step, a free-flow electrophoresis (FFE) step, or any combination thereof.

The exosome isolation procedure may include typical techniques used for extraction of proteins and nucleic acids. For example, the procedure may include, but is not limited to, biomagnetic separation techniques, immunoprecipitation techniques, electrophoretic methods (such as polyacrylamide gel electrophoresis (PAGE), or native gel electrophoresis), chromatographic methods (such as ion exchange chromatography, size-exclusion or gel-permeation chromatography, or affinity chromatography), fractionation methods (such as ultracentrifugation, low-pressure liquid chromatography, or solid phase extraction). In a particular embodiment, the isolation technique is a biomagnetic separation technique using bioparticles such as magnetic microspheres or magnetic nanospheres.

Once an isolated exosome sample has been prepared, the contents of the exosome may be extracted for further study and characterization. Biological material which may be extracted from exosomes includes but is not limited to proteins, peptides, RNA and DNA, lipids and sugars. For example the mirVana™ microRNA Isolation Kit (Life technologies, Frederick, Md.) may be used to recover RNA species, including small RNAs such as microRNA, from exosomes. Total RNA may also be isolated using, for example, other known extraction techniques, such as those employing acid-phenol:chloroform extraction.

The RNAs within the isolated adipocyte-derived exosomes can be analyzed using, for example, sequencing, or nucleotide array analysis. The analysis may comprise analyzing the presence, absence and/or amount of the RNAs within isolated adipocyte-derived exosomes with respect to a panel of pre-determined microRNAs. The panel may contain, for example, at least 1, 2, 3, 4, 5, 6, 7, 8, 9, 10, 15, 20, 30, 40, 50, 75, 100, 150, 200, 250, 300, 400, 500, 1,000, 2,000, or at least 3,000 individual microRNAs of interest.

A marker of the present invention is at least one marker selected from the group consisting of Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, N-acetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4). Preferably, the marker is FABP4.

The marker specific for adipocyte-derived exosomes and the binding agent form a complex. Preferably, the binding agent comprises an anti-FABP4 antibody or antigen-binding fragment thereof.

Methods of Detection

In second aspect of the invention, a method of detecting an obesity-related disorder in a subject is provided, comprising obtaining a biological sample from a subject which contains adipocyte-derived exosomes, isolating adipocyte-derived exosomes from the biological sample using a binding agent which binds to at least one marker specific for adipocyte-derived exosomes, and detecting the presence or absence of an obesity-related disorder based on a measurable (i.e., detectable) change in a profile of the isolated adipocyte-derived exosomes from the subject relative to a profile of the adipocyte-derived exosomes from the control subject.

A profile of isolated adipocyte-derived exosomes from the subject may be a profile of the microRNAs, proteins, mRNAs, lipids, sugars, nucleic acids, or any combination thereof, present in the isolated adipocyte-derived exosomes of the subject. When the profile of isolated adipocyte-derived exosomes from the subject is a microRNA expression profile, the profile comprises an expression level of at least one protein or a combination of proteins present in the isolated adipocyte-derived exosomes of the subject. When the profile of isolated adipocyte-derived exosomes from the subject is an mRNA expression profile, the profile comprises an expression level of at least one mRNA present in the isolated adipocyte-derived exosomes of the subject. When the profile of isolated adipocyte-derived exosomes from the subject is a lipid profile, the profile comprises at least one lipid present in the isolated adipocyte-derived exosomes of the subject. When the profile of isolated adipocyte-derived exosomes from the subject is a sugar profile, the profile comprises at least one sugar present in the isolated adipocyte-derived exosomes of the subject. When the profile of isolated adipocyte-derived exosomes from the subject is a nucleic acid expression profile, the profile comprises an expression level of at least one nucleic acid present in the isolated adipocyte-derived exosomes of the subject.

A profile of the isolated adipocyte-derived exosomes from the subject may be an expression level of at least one protein or a combination of proteins present in the adipocyte-derived exosomes, such as tetraspanins and adipocyte or pre-adipocyte surface markers. Alternatively, a profile of the isolated adipocyte-derived exosomes from the subject may be a nucleic acid expression profile of at least one nucleic acid present in the adipocyte-derived exosomes such as mRNA, microRNA or other RNA species.

Preferably, a profile of the isolated adipocyte-derived exosomes from the subject is an microRNA expression profile comprising an expression level of at least one microRNA present in the adipocyte-derived exosomes. The microRNA expression profile provides the expression level of at least one microRNA or a combination of microRNAs present in the adipocyte-derived exosomes.

More preferably, the profile of isolated adipocyte-derived exosomes from the subject is an microRNA expression profile comprising an expression level of at least one microRNA including, but not limited to, miR-33a, miR-10b, miR-20a, miR-374b, miR-504, miR-101-1, let-7a-5p, and miR-16-5p.

Similarly, a profile of the adipocyte-derived exosomes from a control subject may be a profile of the microRNAs, proteins, mRNAs, lipids, sugars, nucleic acids, or any combination thereof, present in the adipocyte-derived exosomes of the control subject.

The profile of the adipocyte-derived exosomes from the control subject corresponds to the profile of isolated adipocyte-derived exosomes from the subject. The microRNA expression profile, mRNA expression profile, protein expression profile, lipid profile, sugar profile or nucleic acid profile or a combination thereof, of adipocyte-derived exosomes obtained from a subject may be compared to the corresponding microRNA expression profile, mRNA expression profile, protein expression profile, lipid profile, sugar profile or nucleic acid profile or a combination thereof, of adipocyte-derived exosomes from a control subject. For example, when the profile of isolated adipocyte-derived exosomes from the subject is an microRNA expression profile comprising an expression level of at least one microRNA, the profile of adipocyte-derived exosomes of the control subject is also an microRNA expression profile comprising an expression level of at least one microRNA, and the expression level of the at least one microRNA in the microRNA expression profile of the control subject corresponds to the expression level of at least one microRNA in the microRNA expression profile of the subject.

A profile of the isolated adipocyte-derived exosomes from a subject is applied against a profile of adipocyte-derived exosomes from a control subject, and the presence or absence of an obesity-related disorder in the subject is detected based on a measurable or detectable change in the profile of the isolated adipocyte-derived exosomes from the subject relative to the profile of adipocyte-derived exosomes from the control subject.

In some embodiments, a profile of the isolated adipocyte-derived exosomes from a subject is applied against a profile of adipocyte-derived exosomes from a control subject, wherein the profile of the isolated adipocyte-derived exosomes from the subject is an microRNA expression profile comprising an expression level of at least one microRNA present in the adipocyte-derived exosomes of the subject, and the profile of the adipocyte-derived exosomes from the control subject is an microRNA expression profile comprising an expression level of at least one microRNA present in the adipocyte-derived exosomes of the control subject. In such case, at least one microRNA in the microRNA expression profile from the subject is compared to the corresponding at least one microRNA in the microRNA expression profile from the control subject. A measurable or detectable change in the expression level of at least one microRNA in the profile of the isolated adipocyte-derived exosomes from the subject relative to the corresponding expression level of at least one microRNA in the profile of the adipocyte-derived exosomes from the control subject indicates the presence or absence of an obesity related-disorder. In one embodiment, the expression level of the at least one microRNA from the subject may be higher relative to the corresponding expression level of the at least one microRNA from the control subject. In another embodiment, the expression level of the at least one microRNA from the subject may be lower relative to the corresponding expression level of the at least one microRNA from the control subject.

The method may further include applying a profile of the isolated adipocyte-derived exosomes from the subject against a profile of adipocyte-derived exosomes from a control subject.

The detection method further includes diagnosing the subject as having an obesity-related disorder.

In another embodiment, the detection method may further include determining the profile of the isolated adipocyte-derived exosomes.

In yet another embodiment, the detection method may further include administering at least one therapeutic agent to the subject to treat an obesity-related disorder.

In still another embodiment, the detection method may further include recommending to the subject, a therapy comprising a therapeutic regimen, a surgical intervention, a behavioral modification, or a combination thereof.

In a third aspect of the present invention, a method of detecting an increased risk of a subject for having obesity-related disorder is provided, comprising
obtaining a biological sample from a subject which contains adipocyte-derived exosomes,
isolating adipocyte-derived exosomes from the biological sample using a binding agent which binds to at least one marker specific for adipocyte-derived exosomes, and
detecting an increased risk of having obesity-related disorder based on a measurable (i.e., detectable) change in the profile of the isolated adipocyte-derived exosomes from the subject relative to the profile of the adipocyte-derived exosomes from the control subject.

A profile of isolated adipocyte-derived exosomes from a subject and a profile of adipocyte-derived exosomes from a control subject is as described above.

A profile of the isolated adipocyte-derived exosomes from a subject is applied against a profile of adipocyte-derived exosomes from a control subject, and an increased risk of a subject for having an obesity-related disorder is detected based on a measurable or detectable change in the profile of the isolated adipocyte-derived exosomes from the subject relative to the profile of adipocyte-derived exosomes from the control subject.

In some embodiments, a profile of the isolated adipocyte-derived exosomes from a subject is applied against a profile of adipocyte-derived exosomes from a control subject, wherein the profile of the isolated adipocyte-derived exosomes from the subject is an microRNA expression profile comprising an expression level of at least one microRNA present in the adipocyte-derived exosomes of the subject, and the profile of the adipocyte-derived exosomes from the control subject is an microRNA expression profile comprising an expression level of at least one microRNA present in the adipocyte-derived exosomes of the control subject. In such case, the at least one microRNA in the microRNA expression profile from the subject may be compared to the corresponding at least one microRNA in the microRNA expression profile from the control subject. A measurable or detectable change in the expression level of the at least one microRNA in the profile of the isolated adipocyte-derived exosomes from the subject relative to the corresponding expression level of the at least one microRNA in the profile of the adipocyte-derived exosomes from the control subject indicates an increased risk of the subject having an obesity related-disorder. In one embodiment, the expression level of the at least one microRNA from the subject may be higher relative to the corresponding expression level of the at least one microRNA from the control subject. In another embodiment, the expression level of the at least one microRNA from the subject may be lower relative to the corresponding expression level of the at least one microRNA from the control subject.

The detection method of increased risk may further include applying a profile of the isolated adipocyte-derived exosomes from the subject against a profile of adipocyte-derived exosomes from a control subject.

The detection of increased risk may further include diagnosing the subject as having an obesity-related disorder.

In another embodiment, the detection of increased risk may further include determining the profile of the isolated adipocyte-derived exosomes.

In yet another embodiment, the detection of increased risk may further include administering at least one therapeutic agent to the subject to treat an obesity-related disorder.

In still another embodiment, the detection of increased risk may further include recommending to the subject a therapy comprising a therapeutic regimen, a surgical intervention, a behavioral modification, or a combination thereof.

Method of Screening for or Identification of a Therapy

In a fourth aspect of the present invention, a method for screening or identifying a therapy for an obesity-related disorder for a subject is provided, comprising
obtaining a biological sample from a subject which contains adipocyte-derived exosomes,
isolating adipocyte-derived exosomes from the biological sample using a binding agent which binds to at least one marker specific for adipocyte-derived exosomes,
detecting the subject has an obesity-related disorder or has an increased risk of having an obesity-related disorder, based on a measurable (i.e., detectable) change in the profile of the isolated adipocyte-derived exosomes from the subject relative to the profile of the adipocyte-derived exosomes from the control subject, and
identifying a therapy for the obesity-related disorder.

The therapy identified may include, but is not limited to, a therapeutic regimen, a surgical intervention, a behavioral modification, or a combination thereof, as described above.

The present invention may further include modifying an existing therapy using the detection method described above.

A profile of isolated adipocyte-derived exosomes from the subject and a profile of the adipocyte-derived exosomes from a control subject is as described above.

A profile of the isolated adipocyte-derived exosomes from a subject is applied against a profile of adipocyte-derived exosomes from a control subject, and an increased risk of a subject for having an obesity-related disorder is detected based on a measurable or detectable change in the profile of the isolated adipocyte-derived exosomes from the subject relative to the profile of adipocyte-derived exosomes from the control subject.

In some embodiments, a profile of the isolated adipocyte-derived exosomes from a subject is applied against a profile of adipocyte-derived exosomes from a control subject, wherein the profile of the isolated adipocyte-derived exosomes from the subject is an microRNA expression profile comprising an expression level of at least one microRNA present in the adipocyte-derived exosomes of the subject, and the profile of the adipocyte-derived exosomes from the control subject is an microRNA expression profile comprising an expression level of at least one microRNA present in the adipocyte-derived exosomes of the control subject. In such case, at least one microRNA in the microRNA expression profile from the subject may be compared to the corresponding at least one microRNA in the microRNA expression profile from the control subject. A measurable or detectable change in the expression level of the at least one microRNA in the profile of the isolated adipocyte-derived exosomes from the subject relative to the corresponding expression level of the at least one microRNA in the profile of the adipocyte-derived exosomes from the control subject indicates the presence or absence of an obesity related-disorder, or an increased risk of the subject having an obesity related-disorder. In one embodiment, the expression level of the at least one microRNA from the subject may be higher relative to the corresponding expression level of the at least one microRNA from the control subject. In another embodiment, the expression level of the at least one microRNA from the subject may be lower relative to the corresponding expression level of the at least one microRNA from the control subject.

The screening or identification of a therapy may further include applying a profile of the isolated adipocyte-derived exosomes from the subject against a profile of adipocyte-derived exosomes from a control subject.

The screening or identification of a therapy may further include determining the profile of the isolated adipocyte-derived exosomes.

In another embodiment, the screening or identification of a therapy may further include administering or performing the identified therapy to the subject.

In yet another embodiment, the screening or identification of a therapy may further include recommending the identified therapy to the subject, a therapy comprising a therapeutic regimen, a surgical intervention, a behavioral modification, or a combination thereof.

Method of Screening for or Identification of a Therapeutic Agent

In a fifth aspect of the present invention, a method for identifying at least one therapeutic agent for an obesity-related disorder for a subject is provided, comprising obtaining a biological sample from a subject which contains adipocyte-derived exosomes, isolating adipocyte-derived exosomes from the biological sample using a binding agent which binds to at least one marker specific for adipocyte-derived exosomes, detecting the subject has an obesity-related disorder or has an increased risk of having an obesity-related disorder, based on a measurable (i.e., detectable) change in a profile of the isolated adipocyte-derived exosomes from the subject relative to a profile of the adipocyte-derived exosomes from the control subject, and identifying at least one therapeutic agent for treatment or prevention of the obesity-related disorder.

The therapeutic agent identified may include, but is not limited to, an agent for treatment or prevention of a glucose homeostasis disorder, an agent for treatment or prevention of a respiratory disorder, an agent for treatment or prevention of a cardiovascular disorder, an agent for treatment or prevention of a neoplastic disease, an agent for treatment or prevention of a gallbladder disease, an agent for arthritis, or a combination thereof, as described above.

A profile of isolated adipocyte-derived exosomes from the subject and a profile of the adipocyte-derived exosomes from a control subject is as described above.

A profile of the isolated adipocyte-derived exosomes from a subject is applied against a profile of adipocyte-derived exosomes from a control subject, and detection of an obesity-related disorder or an increased risk of a subject for having an obesity-related disorder is based on a measurable or detectable change in the profile of the isolated adipocyte-derived exosomes from the subject relative to the profile of adipocyte-derived exosomes from the control subject.

in some embodiments, a profile of the isolated adipocyte-derived exosomes from a subject is applied against a profile of adipocyte-derived exosomes from a control subject, wherein the profile of the isolated adipocyte-derived exosomes from the subject is an microRNA expression profile comprising an expression level of at least one microRNA present in the adipocyte-derived exosomes of the subject, and the profile of the adipocyte-derived exosomes from the control subject is an microRNA expression profile comprising an expression level of at least one microRNA present in the adipocyte-derived exosomes of the control subject. In such case, at least one microRNA in the microRNA expression profile from the subject may be compared to the corresponding at least one microRNA in the microRNA expression profile from the control subject. A measurable or detectable change in the expression level of the at least one microRNA in the profile of the isolated adipocyte-derived exosomes from the subject relative to the corresponding expression level of the at least one microRNA in the profile of the adipocyte-derived exosomes from the control subject indicates the presence or absence of an obesity related-disorder, or an increased risk of the subject having an obesity related-disorder. In one embodiment, the expression level of the at least one microRNA from the subject may be higher relative to the corresponding expression level of the at least one microRNA from the control subject. In another embodiment, the expression level of the at least one microRNA from the subject may be lower relative to the corresponding expression level of the at least one microRNA from the control subject.

The screening for or identification of at least one therapeutic agent may further include applying a profile of the isolated adipocyte-derived exosomes from the subject against a profile of adipocyte-derived exosomes from a control subject.

The screening for or identification of at least one therapeutic agent may further include determining the profile of the isolated adipocyte-derived exosomes.

In another embodiment, the screening for or identification of at least one therapeutic agent may further include administering the at least one therapeutic agent to the subject.

In yet another embodiment, the screening for or identification of at least one therapeutic agent may further include recommending the at least one therapeutic agent to the subject.

Method of Treatment or Prevention

In a sixth aspect of the present invention, a method for identifying at least one therapeutic agent for an obesity-related disorder for a subject is provided, comprising obtaining a biological sample from a subject which contains adipocyte-derived exosomes, isolating adipocyte-derived exosomes from the biological sample using a binding agent which binds to at least one marker specific for adipocyte-derived exosomes, detecting the subject has an obesity-related disorder or has an increased risk of having an obesity-related disorder, based on a measurable (i.e., detectable) change in a profile of the isolated adipocyte-derived exosomes from the subject relative to a profile of the adipocyte-derived exosomes from the control subject, and administering a therapy to the subject.

The therapy may include, but is not limited to, a therapeutic regimen, a surgical intervention, a behavioral modification, or a combination thereof, as described above.

A profile of isolated adipocyte-derived exosomes from the subject and a profile of the adipocyte-derived exosomes from a control subject is as described above.

A profile of the isolated adipocyte-derived exosomes from a subject is applied against a profile of adipocyte-derived exosomes from a control subject, and detection of an obesity-related disorder or an increased risk of a subject for having an obesity-related disorder is based on a measurable or detectable change in the profile of the isolated adipocyte-derived exosomes from the subject relative to the profile of adipocyte-derived exosomes from the control subject.

Preferably, a profile of the isolated adipocyte-derived exosomes from a subject is applied against a profile of adipocyte-derived exosomes from a control subject, wherein the profile of the isolated adipocyte-derived exosomes from the subject is an microRNA expression profile comprising an expression level of at least one microRNA present in the adipocyte-derived exosomes of the subject, and the profile of the adipocyte-derived exosomes from the control subject is an microRNA expression profile comprising an expression level of at least one microRNA present in the adipocyte-derived exosomes of the control subject. In such case, at least one microRNA in the microRNA expression profile from the subject may be compared to the corresponding at least one microRNA in the microRNA expression profile from the control subject. A measurable or detectable change in the expression level of the at least one microRNA in the profile of the isolated adipocyte-derived exosomes from the subject relative to the corresponding expression level of the at least one microRNA in the profile of the adipocyte-derived exosomes from the control subject indicates the presence or absence of an obesity related-disorder, or an increased risk of the subject having an obesity related-disorder. In one embodiment, the expression level of the at least one microRNA from the subject may be higher relative to the corresponding expression level of the at least one microRNA from the control subject. In another embodiment, the expression level of the at least one microRNA from the subject may be lower relative to the corresponding expression level of the at least one microRNA from the control subject.

The method of treatment or prevention may further include applying a profile of the isolated adipocyte-derived exosomes from the subject against a profile of adipocyte-derived exosomes from a control subject.

The method of treatment or prevention may further include determining the profile of the isolated adipocyte-derived exosomes.

The method of treatment or prevention may further include identification of at least one therapeutic agent.

In yet another embodiment, the method of treatment or prevention may further include may further include recommending a therapy to the subject.

Isolating FABP4+ Adipocyte-Derived Exosomes

In one aspect of the present invention, a method of isolating FABP4+ adipocyte-derived exosomes is provided, comprising:

obtaining a biological sample from a human subject which contains FABP4+ adipocyte-derived exosomes;

isolating the FABP4+ adipocyte-derived exosomes from the biological sample using an anti-FABP4+ antibody;

wherein the biological sample is blood, serum, or urine; and wherein the FABP4+ adipocyte-derived exosomes are isolated using magnetic beads.

Detection an Obesity-Related Disorder

In another aspect of the present invention, a method of detecting an obesity-related disorder is provided, comprising:

obtaining a biological sample from a human subject which contains FABP4+ adipocyte-derived exosomes;

isolating the FABP4+ adipocyte-derived exosomes from the biological sample using a FABP4+ antibody; and detecting the human subject has an obesity-related disorder based on a measurable or detectable change in an expression level of at least one microRNA in a profile of the isolated FABP4+ adipocyte-derived exosomes from the human subject relative to a corresponding expression level of at least one microRNA in a profile of FABP4+ adipocyte-derived exosomes from a control human subject;

wherein the biological sample is blood, serum, or urine;

wherein the FABP4+ adipocyte-derived exosomes are isolated using magnetic beads;

wherein the expression level of at least one microRNA in the microRNA expression profile of isolated FABP4+ adipocyte-derived exosomes from the human subject is higher relative to the corresponding expression level of at least one microRNA in the microRNA expression profile of FABP4+ adipocyte-derived exosomes from the control subject.

The detection method may further include applying a profile of the isolated FABP4+ adipocyte-derived exosomes from the subject against a profile of FABP4+ adipocyte-derived exosomes from a control subject.

The detection method may further include determining the profile of the isolated FABP4+ adipocyte-derived exosomes.

The detection method may further include identification of at least one therapeutic agent.

The detection method may further include may further include recommending a therapy to the subject.

Detection an Increased Risk of Having an Obesity-Related Disorder

In another aspect of the present invention, a method of detecting an increased risk of a subject for having obesity-related disorder is provided, comprising:

obtaining a biological sample from a human subject which contains FABP4+ adipocyte-derived exosomes;

isolating the FABP4+ adipocyte-derived exosomes from the biological sample using a FABP4+ antibody; and detecting the human subject has an increased risk of having an obesity-related disorder based on a measurable or detectable change in an expression level of at least one microRNA in a profile of the isolated FABP4+ adipocyte-derived exosomes from the human subject relative to a corresponding expression level of at least one microRNA in a profile of FABP4+ adipocyte-derived exosomes from a control human subject;

wherein the biological sample is blood, serum, or urine;

wherein the FABP4+ adipocyte-derived exosomes are isolated using magnetic beads;

wherein the expression level of at least one microRNA in the microRNA expression profile of isolated FABP4+ adipocyte-derived exosomes from the human subject is higher relative to the corresponding expression level of at least one microRNA in the microRNA expression profile of FABP4+ adipocyte-derived exosomes from the control subject.

The detection method may further include applying a profile of the isolated FABP4+ adipocyte-derived exosomes from the subject against a profile of FABP4+ adipocyte-derived exosomes from a control subject.

The detection method may further include determining the profile of the isolated FABP4+ adipocyte-derived exosomes.

The detection method may further include identification of at least one therapeutic agent.

The detection method may further include recommending a therapy to the subject.

Screening for or Identification of a Therapy for an Obesity-Related Disorder

In another aspect of the present invention, a method of screening for or identifying of a therapy for an obesity-related disorder is provided, comprising:

obtaining a biological sample from a human subject which contains FABP4+ adipocyte-derived exosomes;

isolating the FABP4+ adipocyte-derived exosomes from the biological sample using a FABP4+ antibody;

detecting the human subject has an obesity-related disorder or has an increased risk of having an obesity-related disorder based on a measurable or detectable change in an expression level of at least one microRNA in a profile of the isolated FABP4+ adipocyte-derived exosomes from the human subject relative to a corresponding expression level of at least one microRNA in a profile of FABP4+ adipocyte-derived exosomes from a control human subject; and identifying a therapy for the obesity-related disorder;

wherein the biological sample is blood, serum, or urine;

wherein the FABP4+ adipocyte-derived exosomes are isolated using magnetic beads;

wherein the expression level of at least one microRNA in the microRNA expression profile of isolated FABP4+ adipocyte-derived exosomes from the human subject is higher relative to the corresponding expression level of at least one microRNA in the microRNA expression profile of FABP4+ adipocyte-derived exosomes from the control subject.

The method may further include applying a profile of the isolated FABP4+ adipocyte-derived exosomes from the subject against a profile of FABP4+ adipocyte-derived exosomes from a control subject.

The method may further include determining the profile of the isolated FABP4+ adipocyte-derived exosomes.

The method may further include identification of at least one therapeutic agent.

The method may further include recommending a therapy to the subject.

Screening for or Identification of a Therapeutic Agent for an Obesity-Related Disorder In a fifth preferred aspect of the present invention, a method of screening for or identification of at least one therapeutic agent for an obesity-related disorder is provided, comprising:

obtaining a biological sample from a human subject which contains FABP4+ adipocyte-derived exosomes;

isolating the FABP4+ adipocyte-derived exosomes from the biological sample using a FABP4+ antibody;

detecting the human subject has an obesity-related disorder or has an increased risk of having an obesity-related disorder based on a measurable or detectable change in an expression level of at least one microRNA in a profile of the isolated FABP4+ adipocyte-derived exosomes from the human subject relative to a corresponding expression level of at least one microRNA in a profile of FABP4+ adipocyte-derived exosomes from a control human subject; and identifying at least one therapeutic agent for the obesity-related disorder;

wherein the biological sample is blood, serum, or urine;

wherein the FABP4+ adipocyte-derived exosomes are isolated using magnetic beads;

wherein the expression level of at least one microRNA in the microRNA expression profile of isolated FABP4+ adipocyte-derived exosomes from the human subject is higher relative to the corresponding expression level of at least one microRNA in the microRNA expression profile of FABP4+ adipocyte-derived exosomes from the control subject.

The method may further include applying a profile of the isolated FABP4+ adipocyte-derived exosomes from the subject against a profile of FABP4+ adipocyte-derived exosomes from a control subject.

The method may further include determining the profile of the isolated FABP4+ adipocyte-derived exosomes.

The method may further include identification of at least one therapeutic agent.

The method may further include recommending a therapy to the subject.

Method of Treating or Preventing an Obesity-Related Disorder

In a sixth preferred aspect of the present invention, a method for treating or preventing an obesity-related disorder is provided, comprising:

obtaining a biological sample from a human subject which contains FABP4+ adipocyte-derived exosomes;

isolating the FABP4+ adipocyte-derived exosomes from the biological sample using a FABP4+ antibody;

detecting the human subject has an obesity-related disorder or has an increased risk of having an obesity-related disorder based on a measurable or detectable change in an expression level of at least one microRNA in a profile of the isolated FABP4+ adipocyte-derived exosomes from the human subject relative to a corresponding expression level of at least one microRNA in a profile of FABP4+ adipocyte-derived exosomes from a control human subject; and administering a therapy for the obesity-related disorder;

wherein the biological sample is blood, serum, or urine;

wherein the FABP4+ adipocyte-derived exosomes are isolated using magnetic beads; and wherein the expression level of at least one microRNA in the microRNA expression profile of isolated FABP4+ adipocyte-derived exosomes from the human subject is higher relative to the corresponding expression level of at least one microRNA in the microRNA expression profile of FABP4+ adipocyte-derived exosomes from the control subject.

The method may further include applying a profile of the isolated FABP4+ adipocyte-derived exosomes from the subject against a profile of FABP4+ adipocyte-derived exosomes from a control subject.

The method may further include determining the profile of the isolated FABP4+ adipocyte-derived exosomes.

The method may further include identification of at least one therapeutic agent.

The method may further include may further include recommending a therapy to the subject.

Kit

According to a further aspect of the invention, an exosome isolation kit is provided for carrying out the process of the invention. The present invention provides kits for isolating adipocyte-derived exosomes, for detecting, monitoring or diagnosing an obesity-related disorder, for screening for or identification of a subject having such an obesity-related disorder or at increased risk for an obesity-related disorder, for screening for or identification of a therapy or at least one therapeutic agent for possible treatment or monitoring progression (or regression), and for treating or preventing an obesity-related disorder.

The kit typically includes a binding agent capable of specifically binding to a surface marker on an adipocyte-derived exosome as described herein. In some embodiments, the marker is Fatty Acid Binding Protein 4 (FABP4). Other components of the kit may include, but are not limited to, bioparticle such as a magnetic bead or avidin/streptavidin for binding to the binding agent. The kit may optionally include solution(s) for precipitating adipocyte-derived exosome from cells or biological material from a biological sample such as blood/serum or urine sample. The kit may further optionally include reagent(s) for extracting the contents of the exosome (such as proteins, peptides, RNA and DNA, and lipids) for further study and characterization as described herein. The kit may also optionally include packaging material packaging the binding agent capable of specifically binding to a surface marker on an adipocyte-derived exosome and a component such as magnetic beads for binding to the binding agent. The kit may also contain instructions for performing the exosome isolation process of the invention and for preparing the agents or reagents used therein, as well as other accessories useful in carrying out the process.

The kit may include one or more containers, comprising one or more binding agents capable of specifically binding to a surface marker on an adipocyte-derived exosome. Any label on, or associated with, the container(s) indicates that the enclosed composition is used for isolating or diagnosing an obesity-related disease or disorder.

A kit may comprise a carrier being compartmentalized to receive in close confinement therein one or more container means or series of container means such as test tubes, vials, flasks, bottles, syringes, or the like.

The methods and kits of the present invention provide a means for selectively isolating adipocyte-derived exosomes, from cells or biological materials.

Compositions

The present invention further provides a composition comprising a binding agent capable of specifically binding to a surface marker on an adipocyte-derived exosome as described herein. In some embodiments, the marker is Fatty Acid Binding Protein 4 (FABP4).

The composition may optionally further include solution(s) for precipitating adipocyte-derived exosome from cells or biological material from a biological sample.

The kit composition may further optionally include reagent(s) for extracting the contents of the exosome (such as proteins, peptides, RNA and DNA, and lipids) for further study and characterization as described herein.

Having now fully described the invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and may be applied to the essential features hereinbefore set forth.

All references cited herein are hereby incorporated by reference in their entireties, whether previously specifically incorporated or not.

A method for isolating adipocyte-derived exosomes from a subject, comprising obtaining a biological sample from a subject which contains adipocyte-derived exosomes; and isolating adipocyte-derived exosomes from the biological sample using a binding agent which binds to at least one marker specific for adipocyte-derived exosomes.

The method of [225], wherein the at least one marker specific for adipocyte-derived exosomes is selected from the group consisting of Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, Nacetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4).

The method of claim [226], wherein the at least one marker is Fatty Acid Binding Protein 4 (FABP4). The method of [225], wherein said biological sample is not adipose tissue. The method of [225], wherein said biological sample comprises blood or serum. The method of [225], wherein said biological sample comprises urine. The method of [225], wherein the biological sample comprises milk, blood, serum, plasma, ascites, cyst fluid, pleural fluid, peritoneal fluid, cerebral spinal fluid, tears, urine, saliva, sputum, or combinations thereof. The method of [225], wherein the binding agent comprises an anti-FABP4 antibody, or an antigen-binding fragment thereof. The method of [225], wherein the adipocyte-derived exosomes are isolated using magnetic beads. The method of [225], wherein the isolated adipocyte-derived exosomes are substantially free of other non-adipocyte-derived exosomes.

The method of [225], wherein the biological sample is collected from a lean subject, an overweight subject, or an obese subject.

The method of [228], wherein the biological sample is collected from an obese subject prior to initiation of a weight-loss treatment, surgery, or regimen. The method of

[225] wherein the biological sample is collected from an obese subject after initiation or completion of a weight-loss treatment, surgery, or regimen.

A kit for isolating adipocyte-derived exosomes in a biological sample comprising: (a) a binding agent which specifically binds to a marker specific for adipocyte-derived exosomes; (b) a bioparticle for isolation of the adipocyte-derived exosomes; and (c) instructions for performing the adipocyte-derived exosome isolation.

The kit of [230], wherein the marker is at least one marker selected from the group consisting of Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, N-acetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4).

The kit of [230], wherein the bioparticle for isolation of the adipocyte-derived exosomes comprises a magnetic bead or an agarose bead.

The kit of [232], wherein the magnetic bead is at least one magnetic bead selected from the group consisting of a sepharose magnetic bead, a streptavidin magnetic bead, Protein A magnetic bead, Protein G magnetic bead, a ferromagnetic bead, a magnetic nanosphere, a magnetic microsphere, and a polyvinyl alcohol magnetic particle (M-PVA Magnetic Bead).

A kit for isolating adipocyte-derived exosomes in a biological sample comprising: (a) a binding agent which specifically binds to Fatty Acid Binding Protein 4 (FABP4); (b) at least one magnetic bead; and (c) instructions for performing the adipocyte-derived exosome isolation.

A method of detecting an obesity-related disorder in a subject comprising obtaining a biological sample from a subject which contains adipocyte-derived exosomes, isolating adipocyte-derived exosomes from the biological sample using a binding agent which binds to at least one marker specific for adipocyte-derived exosomes, and detecting the subject has an obesity-related disorder by a measurable change in a profile of the isolated adipocyte-derived exosomes from the subject relative to a profile of adipocyte-derived exosomes from a control subject. Also, a method of detecting increased risk of a subject to having an obesity-related disorder comprising obtaining a biological sample from a subject which contains adipocyte-derived exosomes, isolating adipocyte-derived exosomes from the biological sample using a binding agent which binds to at least one marker specific for adipocyte-derived exosomes, detecting the subject has an increased risk of having an obesity-related disorder by a measurable change in a profile of the isolated adipocyte-derived exosomes from the subject relative to a profile of adipocyte-derived exosomes from a control subject.

The methods of [235], further comprising applying the profile of the isolated adipocyte-derived exosomes from the subject against the profile of adipocyte-derived exosomes from the control subject.

The methods of [235], wherein the obesity-related disorder comprises a glucose homeostasis disorder, a respiratory disorder, a cardiovascular disorder, a neoplastic disease, a gallbladder disease, arthritis, dyslipidemia, a mental disorder, a pain syndrome, or a combination thereof.

The methods of [237], wherein the glucose homeostasis disorder is at least one disorder selected from the group consisting of diabetes, insulin resistance, glycosuria, hyperglycemia, hyperinsulinism, and hypoglycemia.

The methods of [238], wherein the glucose homeostasis disorder is diabetes.

The methods of [239], wherein the diabetes is diabetes mellitus type I, diabetes mellitus type II or gestational diabetes.

The methods of [237], wherein the cardiovascular disorder is at least one disorder selected from the group consisting of atherosclerosis, coronary artery disease, stroke, peripheral artery disease, angina, myocardial infarction, hypertension, and hypertensive heart disease.

The methods of [241], wherein the cardiovascular disorder is atherosclerosis.

The methods of [237], wherein the respiratory disorder is at least one disorder selected from the group consisting of asthma, sleep apnea, obesity hypoventilation syndrome and chronic obstructive pulmonary disease.

The methods of [243], wherein the respiratory disorder is asthma.

The methods of [235], wherein the profile of the isolated adipocyte-derived exosomes is selected from the group consisting of an microRNA expression profile, a protein expression profile, an mRNA expression profile, a lipid profile, a sugar profile, and a nucleic acid profile.

The methods of [245], wherein the microRNA expression profile comprises an expression level of at least one microRNA.

The methods of [246], wherein the at least one microRNA is selected from the group consisting of miR-33a, miR-10b, miR-20a, miR-374b, miR-504, miR-101-1, let-7a-5p and miR-16-5p.

The methods of [235], wherein the profile of the isolated adipocyte-derived exosomes from the subject is an microRNA expression profile comprising an expression level of at least one microRNA, and the profile of the adipocyte-derived exosomes from the control subject is an microRNA expression profile comprising an expression level of at least one microRNA; wherein the at least one microRNA in the microRNA expression profile from the subject corresponds to the at least one microRNA in the microRNA expression profile from the control subject; and wherein the expression level of the at least one microRNA from the subject is higher relative to the corresponding expression level of the at least one microRNA from the control subject.

The methods of [235], wherein the profile of the isolated adipocyte-derived exosomes from the subject is an microRNA expression profile comprising an expression level of at least one microRNA, and the profile of the adipocyte-derived exosomes from the control subject is an microRNA expression profile comprising an expression level of at least one microRNA; wherein the at least one microRNA in the microRNA expression profile from the subject corresponds to the at least one microRNA in the microRNA expression profile from the control subject; and wherein the expression level of the at least one microRNA from the subject is lower relative to the corresponding expression level of the at least one microRNA from the control subject.

The methods of [235], wherein the subject is a mammalian subject.

The methods of [250], wherein the mammalian subject is human.

The methods of [235], wherein the biological sample is obtained from a lean subject, an overweight subject, or an obese subject. The methods of [235], the biological sample is obtained from an obese mammalian subject prior to initiation of a weight-loss treatment, surgery, or regimen. The methods of [235], wherein the biological sample is obtained from an obese mammalian subject after initiation or completion of a weight-loss treatment, surgery, or regimen. The methods of [235], wherein said biological sample is not adipose tissue.

The methods of [235], wherein the biological sample comprises milk, blood, serum, plasma, ascites, cyst fluid, pleural fluid, peritoneal fluid, cerebral spinal fluid, tears, urine, saliva, sputum, or combinations thereof.

The methods of [253], wherein the biological sample is blood or serum. The method of [260], wherein the biological sample is urine.

The methods of [235], wherein the at least one marker is selected from the group consisting of Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, Nacetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4).

The methods of [255], wherein the at least one marker is Fatty Acid Binding Protein 4 (FABP4).

The methods of [235], wherein the binding agent comprises an anti-FABP4 antibody, or antigen-binding fragment thereof. The methods of [235], wherein the adipocyte-derived exosomes are isolated using magnetic beads. The methods of [235], wherein the binding agent and the at least one marker specific for adipocyte-derived exosomes form a complex. The methods of [235], further comprising diagnosing the subject as having the obesity-related disorder. The methods of [235], further comprising determining the profile of the isolated adipocyte-derived exosomes. The methods of [235], further comprising administering at least one therapeutic agent to the subject to treat the obesity-related disorder. The methods of [235], further comprising recommending to the subject, a therapy comprising a therapeutic regimen, a surgical intervention, a behavioral modification, or a combination thereof.

A method for identifying a therapy for an obesity-related disorder in a subject comprising: obtaining a biological sample from the subject which contains adipocyte-derived exosomes, isolating adipocyte-derived exosomes from the biological sample using a binding agent which binds to at least one marker specific for adipocyte-derived exosomes, detecting the subject has an obesity-related disorder or has an increased risk of having an obesity-related disorder by a measurable change in a profile of the isolated adipocyte-derived exosomes from the subject relative to a profile of adipocyte-derived exosomes from a control subject, and identifying the therapy for the obesity-related disorder.

The method of [258], further comprising applying the profile of the isolated adipocyte-derived exosomes from the subject against the profile of adipocyte-derived exosomes from the control subject.

The method of [258], wherein the therapy comprises a therapeutic regimen, a surgical intervention, a behavioral modification, or a combination thereof.

The method of [260], wherein the surgical intervention is performing bariatric surgery. The method of [260], wherein the surgical intervention is performing bypass surgery. The method of [260], wherein the therapeutic regimen comprises administering at least one therapeutic agent, a dietary intervention, exercise, or a combination thereof.

The method of [258], wherein the obesity-related disorder is at least one disorder selected from the group consisting of a glucose homeostasis disorder, a respiratory disorder, a cardiovascular disorder, a neoplastic disease, gallbladder disease, arthritis, dyslipidemia, a mental disorder, a pain syndrome, and a combination thereof.

The method of [262], wherein the glucose homeostasis disorder is at least one disorder selected from the group consisting of diabetes, insulin resistance, glycosuria, hyperglycemia, hyperinsulinism, and hypoglycemia.

The method of [263], wherein the glucose homeostasis disorder is diabetes.

The method of [264], wherein the diabetes is selected from the group consisting of diabetes mellitus type I, diabetes mellitus type II and gestational diabetes.

The method of [262], wherein the cardiovascular disorder is at least one disorder selected from the group consisting of atherosclerosis, coronary artery disease, stroke, peripheral artery disease, angina, myocardial infarction, hypertension, and hypertensive heart disease.

The method of [266], wherein the cardiovascular disorder is atherosclerosis.

The method of [262], wherein the respiratory disorder is at least one disorder selected from the group consisting of asthma, sleep apnea, obesity hypoventilation syndrome and chronic obstructive pulmonary disease.

The method of [268], wherein the respiratory disorder is asthma.

The method of [258], wherein the subject is a mammalian subject.

The method of [270], wherein the mammalian subject is human.

The method of [271], wherein the human is lean, overweight, or obese.

The method of [258], wherein the biological sample is obtained from an obese mammalian subject prior to initiation of a weight-loss treatment, surgery, or regimen. The method of [258], wherein the biological sample is obtained from an obese mammalian subject after initiation or completion of a weight-loss treatment, surgery, or regimen. The method of [258], wherein the biological sample is not adipose tissue.

The method of [258], wherein the biological sample comprises milk, blood, serum, plasma, ascites, cyst fluid, pleural fluid, peritoneal fluid, cerebral spinal fluid, tears, urine, saliva, sputum, or combinations thereof.

The method of [274], wherein the biological sample is blood or serum. The method of [275], wherein the biological sample is urine.

The method of [258], wherein the at least one marker is selected from the group consisting of Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVAl, CD137, Shox2, Hoxc8, Hoxc9, Tbx1, Zic1, Lhx8, Tnsfrsf9, Tmem26, UCP-1, Cidea, Prdm16, Nacetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4).

The method of [276], wherein the at least one marker is Fatty Acid Binding Protein 4 (FABP4). The method of [258], wherein the binding agent comprises an anti-FABP4 antibody, or antigen-binding fragment thereof. The method of [258], wherein the adipocyte-derived exosomes are isolated using magnetic beads. The method of [258], wherein the binding agent and the at least one marker specific for adipocyte-derived exosomes form a complex.

The method of [258], wherein the profile of the isolated adipocyte-derived exosomes is selected from the group consisting of an microRNA expression profile, a protein expression profile, an mRNA expression profile, a lipid profile, a sugar profile, and a nucleic acid profile.

The method of [278], wherein the profile of the isolated adipocyte-derived exosomes is an microRNA expression profile comprising an expression level of at least one microRNA.

The method of [279], wherein the at least one microRNA is selected from the group consisting of miR-33a, miR-10b, miR-20a, miR-374b, miR-504, miR-101-1, let-7a-5p and miR-16-5p.

The method of [258], wherein the profile of the isolated adipocyte-derived exosomes from the subject is an microRNA expression profile comprising an expression level of at least one microRNA, and the profile of the adipocyte-derived exosomes from the control subject is an microRNA expression profile comprising an expression level of at least one microRNA; wherein the at least one microRNA in the microRNA expression profile from the subject corresponds to the at least one microRNA in the microRNA expression profile from the control subject; and wherein the expression level of the at least one microRNA from the subject is higher than the corresponding expression level of the at least one microRNA from the control subject.

The method of [258], wherein the profile of the isolated adipocyte-derived exosomes from the subject is an microRNA expression profile comprising an expression level of at least one microRNA, and the profile of the adipocyte-derived exosomes from the control subject is an microRNA expression profile comprising an expression level of at least one microRNA; wherein the at least one microRNA in the microRNA expression profile from the subject corresponds to the at least one microRNA in the microRNA expression profile from the control subject; and wherein the expression level of the at least one microRNA from the subject is lower than the corresponding expression level of the at least one microRNA from the control subject.

The method of [258], further comprising determining the profile of the isolated adipocyte-derived exosomes from the subject. The method of [258], further comprising administering the identified therapy to the subject. The method of [258], further comprising recommending the identified therapy to the subject.

A method of identifying at least one therapeutic agent for an obesity-related disorder in a subject comprising: obtaining a biological sample from a subject which contains adipocyte-derived exosomes, isolating adipocyte-derived exosomes from the biological sample using a binding agent which binds to at least one marker specific for adipocyte-derived exosomes, detecting the subject has an obesity-related disorder or an increased risk of having an obesity-related disorder by a measurable change in a profile of the isolated adipocyte-derived exosomes from the subject relative to a profile of adipocyte-derived exosomes from a control subject, and identifying at least one therapeutic agent the obesity-related disorder.

The method of [283], further comprising applying the profile of the isolated adipocyte-derived exosomes from the subject against the profile of adipocyte-derived exosomes from the control subject.

The method of [283], wherein the at least one therapeutic agent comprises an agent for treatment or prevention of a glucose homeostasis disorder, an agent for treatment or prevention of a respiratory disorder, an agent for treatment or prevention of a cardiovascular disorder, an agent for treatment or prevention of a neoplastic disease, an agent for treatment or prevention of a gallbladder disease, an agent for arthritis, an agent for dyslipidemia, an agent for a mental disorder, an agent for a pain syndrome, or a combination thereof.

The method of [285], wherein the agent for treatment or prevention of a glucose homeostasis disorder comprises orlistat, lorcaserin, phentermine, liraglutide, insulin, amylin, leptin, glucagon, glucagon-like peptide (GLP-1), glucagon-like peptide (GLP-1) receptor agonist, a sulfonylurea, a biguanide, somatostatin, diazoxide, a sodium-glucose cotransporter 2 (SGLT-2) inhibitor, acarbose, miglitol, a dopamine agonist, a dipeptidyl peptidase 4 (DPP-4) inhibitor, a meglitinide, an α-glucosidase inhibitor, a thiazolidinedione, or a combination thereof.

The method of [285], wherein the agent for treatment or prevention of a cardiovascular disorder comprises aldosterone receptor antagonist, an angiotensin II receptor antagonist, an angiotensin converting enzyme inhibitor, a β-adrenergic receptor antagonist, a calcium channel blocker, an $α_2$-adrenergic receptor agonist, an $α_1$-adrenergic receptor antagonist, a vasodilator, a cardiac glycoside, a diuretic, an inotropic agent, a phosphodiesterase inhibitor, an antiarrhythmic agent, potassium, a proprotein convertase subtilisin kexin type 9 (PCSK9) inhibitor, a nitrate, warfarin, a cholesterol lowering agent, or a combination thereof.

The method of [285], wherein the at least one therapeutic agent for treatment or prevention of a respiratory disorder comprises a β-adrenergic receptor agonist, an antihistamine, a leukotriene modifier, a mast cell stabilizer, theophylline, an immunomodulator, an anticholinergic, and a corticosteroid, or a combination thereof.

The method of [283], wherein the profile of the isolated adipocyte-derived exosomes is selected from the group consisting of an microRNA expression profile, a protein expression profile, an mRNA expression profile, a lipid profile, a sugar profile, and a nucleic acid profile.

The method of [289], wherein the microRNA expression profile comprises an expression level of at least one microRNA.

The method of [289], wherein the at least one microRNA is selected from the group consisting of miR-33a, miR-10b, miR-20a, miR-374b, miR-504, miR-101-1, let-7a-5p and miR-16-5p.

The method of [283], wherein the profile of the isolated adipocyte-derived exosomes from the subject is an microRNA expression profile comprising an expression level of at least one microRNA, and the profile of the adipocyte-derived exosomes from the control subject is an microRNA expression profile comprising an expression level of at least one microRNA; wherein the at least one microRNA in the microRNA expression profile from the subject corresponds to the at least one microRNA in the microRNA expression profile from the control subject; and wherein the expression level of the at least one microRNA from the subject is higher than the corresponding expression level of the at least one microRNA from the control subject. The method of [283], wherein the profile of the isolated adipocyte-derived exosomes from the subject is an microRNA expression profile comprising an expression level of at least one microRNA, and the profile of the adipocyte-derived exosomes from the control subject is an microRNA expression profile comprising an expression level of at least one microRNA; wherein the at least one microRNA in the microRNA expression profile from the subject corresponds to the at least one microRNA in the microRNA expression profile from the control subject; and wherein the expression level of the at least one microRNA from the subject is lower than the corresponding expression level of the at least one microRNA from the control subject.

The method of [283], wherein the subject is a mammalian subject.

The method of [293], wherein the mammalian subject is human.

The method of [294], wherein the human is lean, overweight, or obese.

The method of [283], the biological sample is obtained from an obese mammalian subject prior to initiation of a weight-loss treatment, surgery, or regimen. The method of [283], wherein the biological sample is obtained from an obese mammalian subject after initiation or completion of a weight-loss treatment, surgery, or regimen. The method of [283], wherein the biological sample is not adipose tissue.

The method of [283], wherein the biological sample comprises milk, blood, serum, plasma, ascites, cyst fluid, pleural fluid, peritoneal fluid, cerebral spinal fluid, tears, urine, saliva, sputum, or combinations thereof.

The method of [297], wherein the biological sample is blood or serum. The method of [301], wherein the biological sample is urine.

The method of [283], wherein the at least one marker is selected from the group consisting of Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, Nacetyltransferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4).

The method of [299], wherein the at least one marker is Fatty Acid Binding Protein 4 (FABP4).

The method of [283], wherein the binding agent comprises an anti-FABP4 antibody, or antigen-binding fragment thereof. The method of [283], wherein the adipocyte-derived exosomes are isolated using magnetic beads. The method of [283], wherein the binding agent and the at least one marker specific for adipocyte-derived exosomes form a complex. The method of [283], further comprising determining the profile of the isolated adipocyte-derived exosomes from the subject. The method of [283], further comprising administering the at least one therapeutic agent to the subject. The method of [283], further comprising recommending the at least one therapeutic agent to the subject.

A method of treating or preventing an obesity-related disorder in a subject comprising obtaining a biological sample from a subject which contains adipocyte-derived exosomes, isolating adipocyte-derived exosomes from the biological sample using a binding agent which binds to at least one marker specific for adipocyte-derived exosomes, detecting the subject has an obesity-related disorder or an increased risk of having an obesity-related disorder by a measurable change in a profile of the isolated adipocyte-derived exosomes from the subject relative to a profile of adipocyte-derived exosomes from a control subject, and administering a therapy to the subject for the obesity-related disorder.

The method of [302], further comprising applying the profile of the isolated adipocyte-derived exosomes from the subject against the profile of adipocyte-derived exosomes from the control subject.

The method of [302], wherein the therapy comprises a therapeutic regimen, surgical intervention, behavioral modification, or a combination thereof.

The method of [304], wherein the surgical intervention comprises performing bariatric surgery. The method of [304], wherein the surgical intervention comprises performing bypass surgery. The method of [304], wherein the therapeutic regimen comprises administering at least one therapeutic agent, a dietary intervention, exercise, or a combination thereof.

The method of [302], wherein the obesity-related disorder comprises a glucose homeostasis disorder, a respiratory disorder, a cardiovascular disorder, a neoplastic disease, gallbladder disease, arthritis, dyslipidemia, a mental disorder, a pain syndrome, or a combination thereof.

The method of [306], wherein the glucose homeostasis disorder is at least one disorder selected from the group consisting of diabetes, insulin resistance, glycosuria, hyperglycemia, hyperinsulinism, and hypoglycemia.

The method of [307], wherein the glucose homeostasis disorder is diabetes.

The method of [308], wherein the diabetes is diabetes mellitus type I, diabetes mellitus type II, or gestational diabetes.

The method of [306], wherein the cardiovascular disorder is at least one disorder selected from the group consisting of atherosclerosis, coronary artery disease, stroke, peripheral artery disease, angina, myocardial infarction, hypertension, and hypertensive heart disease.

The method of [310], wherein the cardiovascular disorder is atherosclerosis.

The method of [306], wherein the respiratory disorder is at least one disorder selected from the group consisting of asthma, sleep apnea, obesity hypoventilation syndrome and chronic obstructive pulmonary disease.

The method of [312], wherein the respiratory disorder is asthma.

The method of [302], wherein the profile of the isolated adipocyte-derived exosomes is selected from the group consisting of an microRNA expression profile, a protein expression profile, an mRNA expression profile, a lipid profile, a sugar profile, and a nucleic acid profile.

The method of [314], wherein the microRNA expression profile comprises an expression level of at least one microRNA.

The method of [315], wherein the at least one microRNA is selected from the group consisting of miR-33a, miR-10b, miR-20a, miR-374b, miR-504, miR-101-1, let-7a-5p and miR-16-5p.

The method of [302], wherein the profile of the isolated adipocyte-derived exosomes from the subject is an microRNA expression profile comprising an expression level of at least one microRNA, and the profile of the adipocyte-derived exosomes from the control subject is an microRNA expression profile comprising an expression level of at least one microRNA; wherein the at least one microRNA in the microRNA expression profile from the subject corresponds to the at least one microRNA in the microRNA expression profile from the control subject; and wherein the expression level of the at least one microRNA from the subject is higher than the corresponding expression level of the at least one microRNA from the control subject. The method of [302], wherein the profile of the isolated adipocyte-derived exosomes from the subject is an microRNA expression profile comprising an expression level of at least one microRNA, and the profile of the adipocyte-derived exosomes from the control subject is an microRNA expression profile comprising an expression level of at least one microRNA; wherein the at least one microRNA in the microRNA expression profile from the subject corresponds to the at least one microRNA in the microRNA expression profile from the control subject; and wherein the expression level of the at least one microRNA from the subject is higher than the corresponding expression level of the at least one microRNA from the control subject.

The method of [302], wherein the subject is a mammalian subject.

The method of [318], wherein the mammalian subject is human.

The method of [302], wherein the biological sample is obtained from a lean subject, an overweight subject, or an obese subject. The method of [302], the biological sample is obtained from an obese mammalian subject prior to initiation of a weight-loss treatment, surgery, or regimen. The method of [302], wherein the biological sample is obtained from an obese mammalian subject after initiation or completion of a weight-loss treatment, surgery, or regimen. The method of [302], wherein said biological sample is not adipose tissue.

The method of [302], wherein the biological sample comprises milk, blood, serum, plasma, ascites, cyst fluid, pleural fluid, peritoneal fluid, cerebral spinal fluid, tears, urine, saliva, sputum, or combinations thereof.

The method of [321], wherein the biological sample is blood or serum. The method of [321], wherein the biological sample is urine.

The method of [302], wherein the at least one marker is selected from the group consisting of Fatty Acid Binding Protein 4 (FABP4), Pref-1, amino acid transporter Asc-1, proton amino acid transporter PAT-2, purinergic receptor 2X, ligand-gated ion channel 5 (P2RX5), leptin, EBF3, FBX031, EVA1, CD137, Shox2, Hoxc8, Hoxc9, Tbx1, Zic1, Lhx8, Tnsfrsf9, Tmem26, UCP-1, Cidea, Prdm16, Nacetyl-transferase 8-like (Nat8L), prolactin receptor (PRLR), neuregulin-4 (Nrg4), transmembrane protein 120B (Tmem120B), adrenergic β3 receptor (Adrb3), aquaporin-7 (Aqp7), G protein-coupled receptor 81 (Grpr81), G protein-coupled receptor 119 (Gpr119), fatty acid transporter (SLC27a1/FATP1), solute carrier family 7 member 10 (SLC7a10/Asc-1 neutral amino acid transporter), mitochondrial protein uncoupling protein-1 (UCP-1), CD300LG, tetraspanin 18 (tspan18), and frizzled-4 (Fzd4).

The method of [323], wherein the at least one marker is Fatty Acid Binding Protein 4 (FABP4).

The method of [302], wherein the binding agent comprises an anti-FABP4 antibody, or antigen-binding fragment thereof. The method of [302], wherein the adipocyte-derived exosomes are isolated using magnetic beads. The method of [302], wherein the binding agent and the at least one marker specific for adipocyte-derived exosomes form a complex. The method of [302], further comprising determining the profile of the isolated adipocyte-derived exosomes.

EXAMPLES

Example 1

Isolation of Adipocyte-Derived Exosomes from Urine and Blood/Plasma.

Adipocyte-derived exosomes were isolated from the blood/plasma and the urine of human subjects. The blood/plasma and urine samples were either previously frozen, or fresh (i.e., not-previously frozen).

To selectively isolate adipocyte-derived exosomes, exosomes in the blood/serum or urine sample were first precipitated using the ExoQuick®-TC Exosome Precipitation Solution (System Biosciences, Mountain View, Calif.). If frozen, the blood/serum or urine sample was first thawed at room temperature and then centrifuged at 3000×g (6066 rpm on a benchtop centrifuge, r=7.3 cm) for 15 minutes to remove cells and cellular debris. The supernatant was harvested and then added to the ExoQuick®-TC Exosome Precipitation solution; the resulting mixture was mixed thoroughly, and incubated for at least 12 hours at 4° C. Following this incubation, the mixture was centrifuged (1500×g for 30 minutes), and the supernatant was discarded. The pellet was again centrifuged (1500×g for 5 minutes), and excess supernatant was removed (so as to leave about 100 μl of supernatant with the pellet). The pellet was then re-suspended in Phosphate-Buffered Saline (PBS) (by adding about 100 μl PBS).

Figure 6:
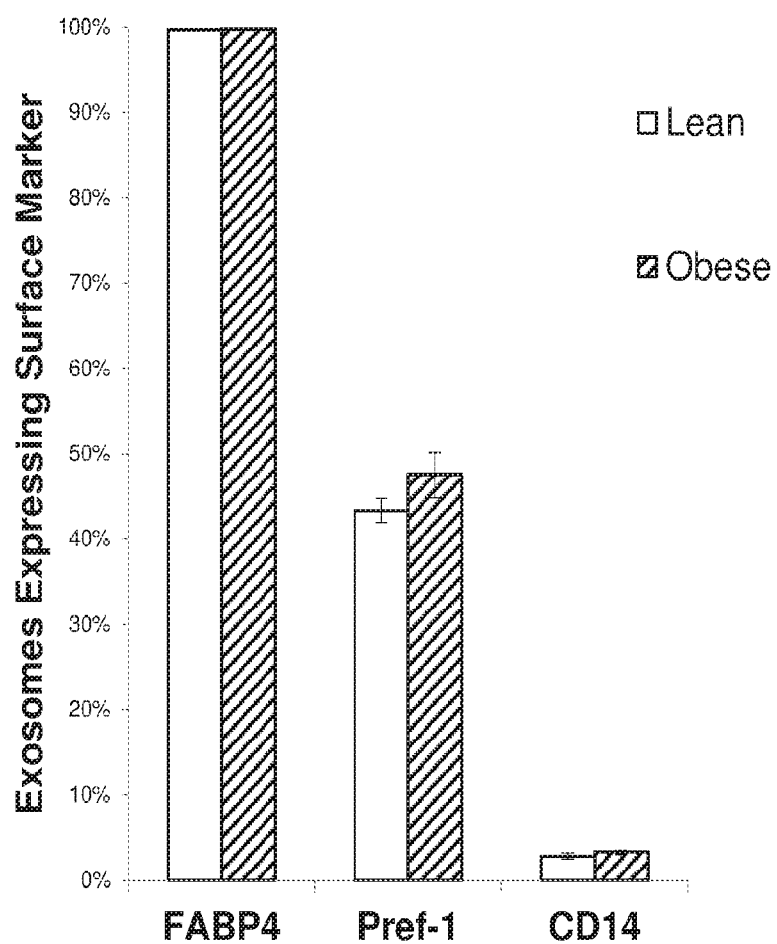
FIG. 6 depicts the proportion of adipocyte-derived exosomes, isolated from lean and obese subjects, expressing the surface markers FABP4, Pref-1 and CD14.

A positive-selection cocktail was produced for the Easy-Sep® "Do-It-Yourself" Selection Kit, in accordance with the manufacturer's directions, using an antibody specific for Fatty Acid Binding Protein 4 (FABP4). FABP4 was used as a selectable marker for adipocyte-derived exosomes, as it was determined that this surface marker was expressed on essentially all adipocyte-derived exosomes. See FIG. 6. The positive-selection cocktail was then added to the PBS-exosome suspension, mixed, and incubated (15 minutes). After this incubation, EasySep® Magnetic Nanoparticles were added and mixed to ensure a uniform suspension. After a short incubation (10 minutes), the suspension was diluted with PBS (2 mL), and the tube containing the suspension was placed beside a magnet to localize the magnetic beads to the inside surface of the tube, and the supernatant was removed, thereby removing non-magnetically-labeled material. The tube was then removed from the magnet, and the magnetic beads in the tube were suspended in PBS. This magnetic selection step was then repeated an additional two times. After these magnetic selection steps, a substantially pure population of adipocyte-derived exosomes was obtained. These exosomes were then frozen before microRNA isolation, if necessary.

Example 2

Isolation of microRNA from the Adipocyte-Derived Exosomes Obtained from Urine and Blood/Serum. Total RNA from the adipocyte-derived exosomes purified above was then isolated using the mirVana™ microRNA Isolation Kit (Life technologies, Frederick, Md.), in accordance with the manufacturer's directions. For some experiments, the extracted RNA was then amplified using the Complete Seramir® Exosome RNA Amplification Kit from Media and Urine (System Biosciences, Mountain View, Calif.) according to the manufacturer's directions, and RNA quality was measured using an Agilent® 2100 Bioanalyzer RNA Pico Chip (Agilent Technologies, Santa Clara, Calif.). Information on the type and abundance of RNAs in the adipocyte-derived exosomes was then determined using microarray analysis.

Example 3

Diabetes

Pre- vs. Post-Bypass Surgery microRNA Profiles 168 known mature microRNAs were differentially expressed after surgery in circulating adipocyte-derived exosomes compared with pre-surgery baseline. Once a conservative filter was applied (only microRNAs with experimentally confirmed or highly conserved predicted targets), 56 microRNAs remained, which collectively putatively targeted 7,143 mRNAs.

Using the 7,143 mRNA targets of the 56 surgery-responsive microRNAs, Ingenuity Pathway Analysis Suite was used to identify enriched biological pathways. One of the top canonical pathways identified as enriched was the WNT-Beta Catenin pathway (102 molecules in the dataset/167 molecules in pathway; pathway p value=$1.41E^{-12}$), similar to what was found when analyzing the adipose-derived exosomes isolated directly from the visceral adipose itself. See Kishida, K., et al., *Visceral adiposity as a target for the management of the metabolic syndrome*. Ann Med, 2012. 44(3): p. 233-41. Another top predicted canonical pathway for the pre- to post-surgery analysis was Insulin Receptor Signaling (FIG. 1), with 74/134 elements represented in the affected mRNA target set (pathway p value=$5.65E^{-07}$). microRNA-mRNA pairs related to this pathway are listed in Table 1 (below). The top ranked novel network (interrelated set of 35 genes) nucleated around the node for insulin-like growth factor 1 (network score=17).

TABLE 1

Surgery-responsive microRNAs with mRNA Targets Related to Insulin Signaling.

| Symbol | Seed | p-value | microRNA Fold Change | # Targets in Insulin Signaling | Targets in Insuling Signaling Pathway |
|---|---|---|---|---|---|
| miR-1227-3p | GUGCCAC | 0.02 | 2.23 | 2 | PRKC1, SOCS3 |
| miR-4691-5p | UCCUCCA | 0.03 | 1.98 | 2 | PIK3C3, PRKAG1 |
| miR-219a-5p | GAUUGUC | 0.02 | 1.80 | 8 | GSK3B, OCRL, PIK3C3G, PPP1R14B, RAPGEF1, RHOQ, SHC1 |
| miR-4728-3p | AUGCUGA | 0.02 | 1.64 | 2 | EIF4E, MAPK1 |
| miR-103-3p | GCAGCAU | 0.02 | 1.59 | 8 | CRKL, IRS2, JAK1, PDE3B, PIK3R1, PRKCI, SOS1, SYNJ1 |
| miR-3622a-3p | CACCUGA | 0.04 | 1.54 | 1 | PIK3R6 |
| miR-4749-3p | GCCCCUC | 0.03 | 1.53 | 2 | PRKACA, RAPGEF1 |
| miR-125b-5p | CCCUGAG | 0.01 | 1.50 | 10 | ASIC1, EIF2B2, EIF4EBP1, GRB10, PIK3C2B, PIK3CD, PIK3R5, PPP1CA, RAF1, RHOQ |
| miR-3926 | GGCCAAA | 0.01 | -1.52 | 1 | PRKAR2B |
| miR-224-5p | AAGUCAC | 0.01 | -1.53 | 5 | CBL, CRKL, GSK3B, IRS2, PIK3R3 |
| miR-4723-5p | GGGGGAG | 0.01 | -1.58 | 6 | AKT1, FOXO4, PIK3R2, PRKACA, RRAS, VAMP2 |
| miR-16-5p | AGCAGCA | 0.02 | -1.59 | 27 | AKT3, CRKL, EIF2B5, EIF4E, FOXO1, GRB10, INSR, IRS1, IRS2, KRAS, LIPE, MAP2L1, MAPK3, MRAS, OCRL, PIK2C3A, PIK3R1, PPP1R11, PRKAR2A, RAF1, RAPGEF1, SGK1, SOS1, SOS2, SYNJ1, TRIP10, TSC1 |
| miR-3690 | CCUGGAC | 0.01 | -1.73 | 2 | PIK3R5, SCNN1G |
| miR-208a-3p | UAAGACG | 0.01 | -1.82 | 3 | IRS2, PRKAR1A, SOS2 |
| miR-4716-3p | AGGGGGA | 0.04 | -1.87 | 3 | AKT2 PRKACA, STXBP4 |
| miR-4525 | GGGGGAU | 0.04 | -1.91 | 2 | PRKACA, VAMP2 |
| miR-2355-5p | UCCCCAG | 0.02 | -1.93 | 4 | CBL, FOXO4, PIK3CD, PPP1R3C |
| miR-4782-5p | UCUGGAU | 0.02 | -2.29 | 1 | GYS1 |

*microRNAs listed limited to those with ≥|1.5| fold change from baseline.

Pre- vs. Post-Bypass Surgery microRNA Changes Correlated to Insulin Resistance.

Using Pearson correlational analyses between change in all microRNA levels and change in HOMA from baseline to one year post-surgery, changes in 46 known mature microRNAs were significantly correlated to a change in HOMA. Once a conservative filter was applied (only experimentally confirmed or highly conserved predicted targets), 29 microRNAs remained, which together putatively target 4,266 mRNAs.

Using the 4,266 mRNA targets of the 29 microRNAs that correlated to HOMA changes after surgery, Ingenuity Pathway Analysis Suite was used to identify enriched biological pathways. Insulin Receptor Signaling (FIG. 2) was again identified as being enriched in the dataset, with 52/134 elements represented in the HOMA-correlated mRNA target set (pathway p value=1.27E-10). Specifically, 10 microRNAs that correlated to HOMA each contained ≥3 target mRNAs within the Insulin Receptor Signaling canonical pathway, and are listed in Table 2.

levels. The microRNAs with the most targets in the Insulin Receptor Signaling pathway included let-7a-5p (r=−0.7; 11 targets including INSR, IRS2, and KRAS) and miR-16-5p (r=0.66; 28 targets including INSR, IRS1, and IRS2).

The data showed that circulating adipocyte-derived exosomal microRNAs, with multiple targets within the canonical Insulin Receptor Signaling pathway, were dysregulated following bariatric surgery. Changes in many of these microRNAs significantly correlated with robust clinical improvements in insulin resistance. This is consistent with previous findings which showed obese adolescents have visceral adipocyte-derived exosomes with dysregulated microRNAs that are predicted to impair insulin receptor signaling, suggesting that adipose exosome signaling is partially responsible for dysfunction and can be positively impacted by bariatric surgery. See Ferrante, S. C., et al., "Adipocyte-derived exosomal microRNAs: a novel mechanism for obesity-related disease," *Pediatr Res*, 2015. 77(3): p. 447-54; and Koeck, E. S., et al., "Adipocyte exosomes induce transforming growth factor beta pathway dysregula-

TABLE 2 microRNAs Correlated to Change in HOMA with >3 Insulin Signaling Targets.

| Symbol | Seed | p-value | HOMA r | # Targets in Insulin Signaling | Targets in Insulin Signaling Pathway |
|---|---|---|---|---|---|
| miR-155-5p | UAAUGCU | 0.021 | 0.88 | 11 | CBL, FOXO3, GSK3B, INPP5D, KRAS, PIK3R1, PRKAR1A, PRKCI, RHOQ, RPTOR, SOS1 |
| miR-503-5p | AGCAGCG | 0.045 | 0.82 | 10 | EIF4E, INSR, MAP2K1, OCRL, PIK3C2A, PIK3R1, PPP1R11, RAF1, SGK1, SLC2A4 |
| miR-199a-5p | CCAGUGU | 0.005 | 0.94 | 7 | CBL, GRB10, GSK3B, PIK3CD, PPP1R12A, SLC2A4, SOS2 |
| miR-539-5p | GAGAAAU | 0.005 | 0.94 | 7 | AKT3, EIF4E, FOXO3, INPP5D, MAPK1, PPP1CB, PRKAG2 |
| miR-874-3p | UGCCCUG | 0.012 | 0.91 | 4 | CRK, GSK3B, INPP5B, PPP1CA |
| miR-4664-5p | GGGGUGC | 0.029 | −0.86 | 4 | ACLY, INPP5D, OCRL, PRKAR2A |
| miR-4747-5p | GGGAAGG | 0.030 | −0.86 | 4 | ASIC1, GRB2, RRAS2, SCNN1A |
| miR-516b-5p | UCUGGAG | 0.038 | 0.84 | 3 | CBL, GYS1, PIK3R5 |
| miR-126-3p | CGUACCG | 0.041 | 0.83 | 4 | CRK, CRKL, IRS1, PIK3R2 |
| miR-122-5p | GGAGUGU | 0.047 | 0.82 | 4 | AKT3, CBL, FOXO3, GYS1 |

Bypass Surgery-Induced Weight-Loss and Metabolic Improvements.

To investigate metabolic changes in patients following gastric bypass, metabolomic profiles of amine-containing metabolites were quantified at baseline (2 weeks prior to surgery) and one year following gastric bypass surgery. Metabolites were assessed by ANCOVA over time, and were correlated to HOMA levels and changes in exosomal microRNAs. As branched chain amino acids (BCAAs) have been particularly linked to insulin dysregulation, exosomal microRNAs that correlated to total BCAAs, as measured in our metabolite panel, were identified. Using a p-value <0.05, 135 microRNAs were significantly correlated with BCAA levels pre- and post-surgery. Of these 135, 91 have conservatively mapped mRNA targets, totaling 8,695 mRNA targets. Specifically relating these microRNAs to the Insulin Receptor Signaling canonical pathway, 48 microRNAs targeting 78 mRNAs were significantly correlated to BCAA tion in hepatocytes: a novel paradigm for obesity-related liver disease," *J Surg Res*, 2014. 192(2): p. 268-75.

Significant metabolomic profile changes in the blood of obese patients were also found one year following bypass surgery (see FIGS. 3A-3F). Significant weight reduction following surgery was associated with a significant rise in fasting plasma Gln and decrease in Gln. The plasma Glu/Gln ratio is significantly elevated in the obese and associated with elevated risk for diabetes, (Cheng S, Rhee E P, Larson M G, Lewis G D, McCabe E L, Shen D, Palma M J, Roberts L D, Dejam A, Souza A L, Deik A A, Magnusson M, Fox C S, O'Donnell C J, Vasan R S, Melander O, Clish C B, Gerszten R E, Wang T J: Metabolite profiling identifies pathways associated with metabolic risk in humans. Circulation 2012; 125:2222-2231; the disclosure of which is incorporated herein in its entirety) and thus the increase in Gln and decrease in Glu would normalize this ratio, thereby reducing the risk of diabetes. Similarly, BCAA accumulation is associated with increased insulin resistance, and significant reductions in fasting plasma BCAAs were found in patients following bypass surgery. In animal models of diet-induced obesity, elevation in fasting BCAAs was associated with decreased catabolism in adipose tissue. See Batch B C, Shah S H, Newgard C B, Turer C B, Haynes C, Bain J R, Muehlbauer M, Patel M J, Stevens R D, Appel L J, Newby L K, Svetkey L P: Branched chain amino acids are novel biomarkers for discrimination of metabolic wellness. Metabolism 2013; 62:961-969; McCormack S E, Shaham O, McCarthy M A, Deik A A, Wang T J, Gerszten R E, Clish C B, Mootha V K, Grinspoon S K, Fleischman A: Circulating branched-chain amino acid concentrations are associated with obesity and future insulin resistance in children and adolescents. Pediatr Obes 2013; 8:52-61; and She P, Van Horn C, Reid T, Hutson S M, Cooney R N, Lynch C J: Obesity-related elevations in plasma leucine are associated with alterations in enzymes involved in branched-chain amino acid metabolism. Am J Physiol Endocrinol Metab 2007; 293:E1552-1563; the disclosures of which are incorporated herein in their entirety. A decrease in BCAAs and an associated increase in fasting Gln can also arise from improved muscle catabolism of BCAAs where excess nitrogen can be removed through Gln export. Mittendorfer B, Volpi E, Wolfe R R: Whole body and skeletal muscle glutamine metabolism in healthy subjects (Am J Physiol Endocrinol Metab, 2001, 280:E323-333). This would occur if muscle insulin sensitivity improved following weight loss. Thus, adipocyte-derived exosomal microRNA changes and their subsequent effect on the muscle may drive these changes.

Example 4

Atherosclerosis

One of the hallmarks of cardiovascular disease is atherosclerosis, which is characterized by macrophage cholesterol efflux impairment leading to intracellular accumulation of modified low-density lipoprotein (LDL) and subsequent formation of plaque-forming lipid-rich foam cells. See Michael, D. R., et al., "Differential regulation of macropinocytosis in macrophages by cytokines: implications for foam cell formation and atherosclerosis," *Cytokine*, 2013. 64(1): p. 357-61; and Rohatgi, A., et al., "HDL cholesterol efflux capacity and incident cardiovascular events," *N Engl J Med*, 2014. 371(25): p. 2383-93. Macrophage cholesterol homeostasis is a delicate balance among influx, endogenous synthesis, esterification/hydrolysis and efflux. See Zhang, M., et al., "MicroRNA-27a/b regulates cellular cholesterol efflux, influx and esterification/hydrolysis in THP-1 macrophages," *Atherosclerosis*, 2014. 234(1): p. 54-64. While the link between obesity and atherosclerosis is strong epidemiologically (see Bastien, M., et al., "Overview of epidemiology and contribution of obesity to cardiovascular disease," *Prog Cardiovasc Dis*, 2014. 56(4): p. 369-81; and Gupta, N., et al., "Childhood obesity in developing countries: epidemiology, determinants, and prevention," *Endocr Rev*, 2012. 33(1): p. 48-70). Large variations exist in individual responses to obesity. For example, some patients with high adiposity have normal cardiovascular health, while others with low adiposity have frank atherosclerosis. See Bradshaw, P. T., K. L. Monda, and J. Stevens, "Metabolic syndrome in healthy obese, overweight, and normal weight individuals: the Atherosclerosis Risk in Communities Study," *Obesity* (Silver Spring), 2013. 21(1): p. 203-9. These observations suggest that adipose health or function, not adipose mass per se, is a determinant of obesity-related comorbities. However, tools to assess adipose health/function in relation to the comorbidities are lacking. Adipose-derived exosomes were identified as a potential link between obese adipose tissue and atherosclerosis.

Characterization of Adipose-Derived Exosomes.

Techniques were developed to quantify and characterize exosomes shed by surgically-acquired adipocytes from seven obese (12-17.5 years, BMI: 33-50 kg/m$^2$) and five lean (11-19 years, BMI: 22-25 kg/m$^2$) subjects. Abundant exosomal microRNAs, but no mRNAs, were detected. Comparison of obese vs. lean visceral adipose donors showed 55 differentially-expressed human microRNAs (p<0.05; fold change≥|1.2|). Pathways analysis identified Cholesterol Transport among the top canonical pathways expected to be altered (downregulated) with visceral adiposity based on projected mRNA targets for the 55 differentially expressed microRNAs.[16]

Integrating Obese Adipose-Derived Exosomal microRNA-ome and Cholesterol Transport.

Figure 4A:
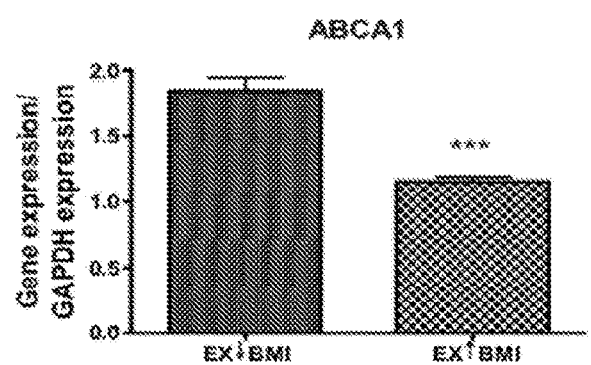
FIGS. 4A-B depict cholesterol transport mRNA changes after adipose-derived exosome exposure. THP-1 macrophages were incubated with obese and lean visceral exosomes for 24 hours. ABCA1, 27-hydroxylase, ABCG1, PPARγ, and LXRα were measured using RT-PCR. Fold changes presented are comparing obese (↑BMI) versus lean (N-BMI) exosome exposures. ABCA1 (FIG. 4A) and 27-hydroxylase (FIG. 4B) are significantly downregulated in response to obese exosome exposure.
Figure 4B:
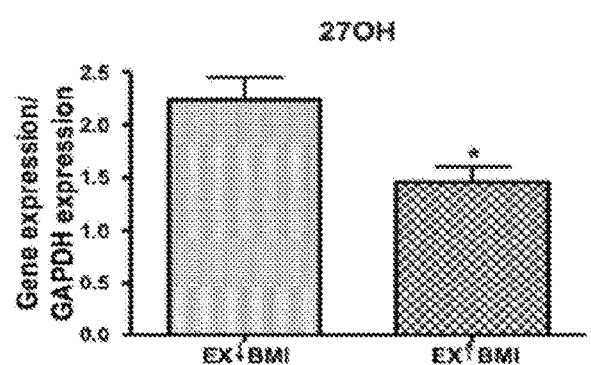

Cholesterol efflux gene expression in naive THP-1 human macrophages were exposed to exosomes derived from adipose tissue of obese (N=5; BMI=39±6) versus lean (N=5; BMI=23±1) age- and sex-matched adolescents (age=15±3 years). THP-1 macrophages were grown for 24 hours in RPMI media in the presence and absence of adipose-derived exosomes (concentration=1 µg/mL). Macrophage mRNA was extracted and reverse transcribed to cDNA. The message level of the cholesterol efflux genes 27-hydroxylase, ABCA1, ABCG1, PPARγ, and LXRα were measured using qRT-PCR. All mRNA expression was normalized to the housekeeping gene GAPDH. Studies were performed in triplicate. ABCA1 mRNA was 30±3% lower (p<0.01) and 27-hydroxylase mRNA was 50±6% lower on exposure to obese (p<0.05) compared to lean exosomes (FIGS. 4A-4B). Additionally, THP-1 ABCG1 mRNA was 53% lower and PPARγ was 48% lower on exposure to obese compared to lean exosomes, although these results did not reach statistical significance. LXRα mRNA did not differ according to exosome exposure. These data suggested that adipose-derived exosomes from obese adolescents reduced macrophage cholesterol efflux gene expression. This demonstrated a novel pro-atherogenic effect on macrophage reverse cholesterol transport genes by adipose-derived exosomes.

microRNA-mRNA Integration

Data for microRNA-mRNA interactions were integrated using miRTarVis (a novel visual analytics tool developed by our collaborative group for integrated analyses of microRNA and mRNA expression profiles with microRNA target prediction algorithms. See Jung, D., et al. 2015. (BioMed Central Ltd., the entirety of which is incorporated by reference herein). Paired expression profiles from obese visceral exosomal (microRNA) and exosome-exposed THP-1 cholesterol efflux genes (mRNA) were used. Six significant (obese vs. lean, p≤0.05) microRNAs: miR-33a, miR-10b*, miR-20a, miR-374b, miR-504, and miR-101-1 present in obese visceral exosomes predicted to target ABCA1, ABCG1, and PPARG were found. These six microRNAs were prioritized for further study with the following filtering criteria: 1) all microRNAs are statistically significant and upregulated in obese vs. lean exosomes (p≤0.05); 2) predicted targets from miRTarVis for cholesterol efflux genes (ABCA1, ABCG1, and PPARG); 3) the majority of microRNAs (four microRNAs out of six) were biologically relevant in the literature. The selected microRNAs are summarized in Table 3.

TABLE 3

| microRNA | Function | Fold Change | p-value | Target Gene(s) |
|---|---|---|---|---|
| miR-33a | Represses cholesterol High-density lipoprotein (HDL) efflux, antagonism has been proven to be a mechanism for increasing HDL and protecting from atherosclerosis. See Fernandez-Hernando, C. and K. J. Moore. (Arterioscler Thromb Vasc Biol, 2011. 31(11): p. 2378-82, the entirety of which is incorporated by reference herein) | 1.17 | 0.024 | ABCA1 PPARG |
| miR-10b* | Directly represses ABCG1 and negatively regulates cholesterol efflux from lipid-loaded macrophages. See Wang, D., et al., (Circ Res, 2012. 111(8): p. 967-81, the entirety of which is incorporated by reference herein). | 1.16 | 0.045 | ABCG1 |
| miR-20a | Involved in macrophage infiltration and activation. See Zhu, D., et al. (J Allergy Clin Immunol, 2013. 132(2): p. 426-36 e8, the entirety of which is incorporated by reference herein); and Chang, R. C., et al., (Cells, 2014. 3(3): p. 702-12, the entirety of which is incorporated by reference herein). | 1.13 | 0.038 | ABCA1 |
| miR-374b | Recent study suggests that miR-374b may play a role in lipid metabolism regulation and interacts with PPARG by down-regulating expression. See Pan, S., et al., (Horm Metab Res, 2013. 45(7): p. 518-25, the entirety of which is incorporated by reference herein). | 1.12 | 0.030 | ABCA1 ABCG1 PPARG |
| miR-504 | Not defined in literature | 1.19 | 0.043 | ABCA1 ABCG1 |
| miR-101-1 | Not defined in literature | 1.21 | 0.049 | ABCA1 PPARG |

Figure 2:
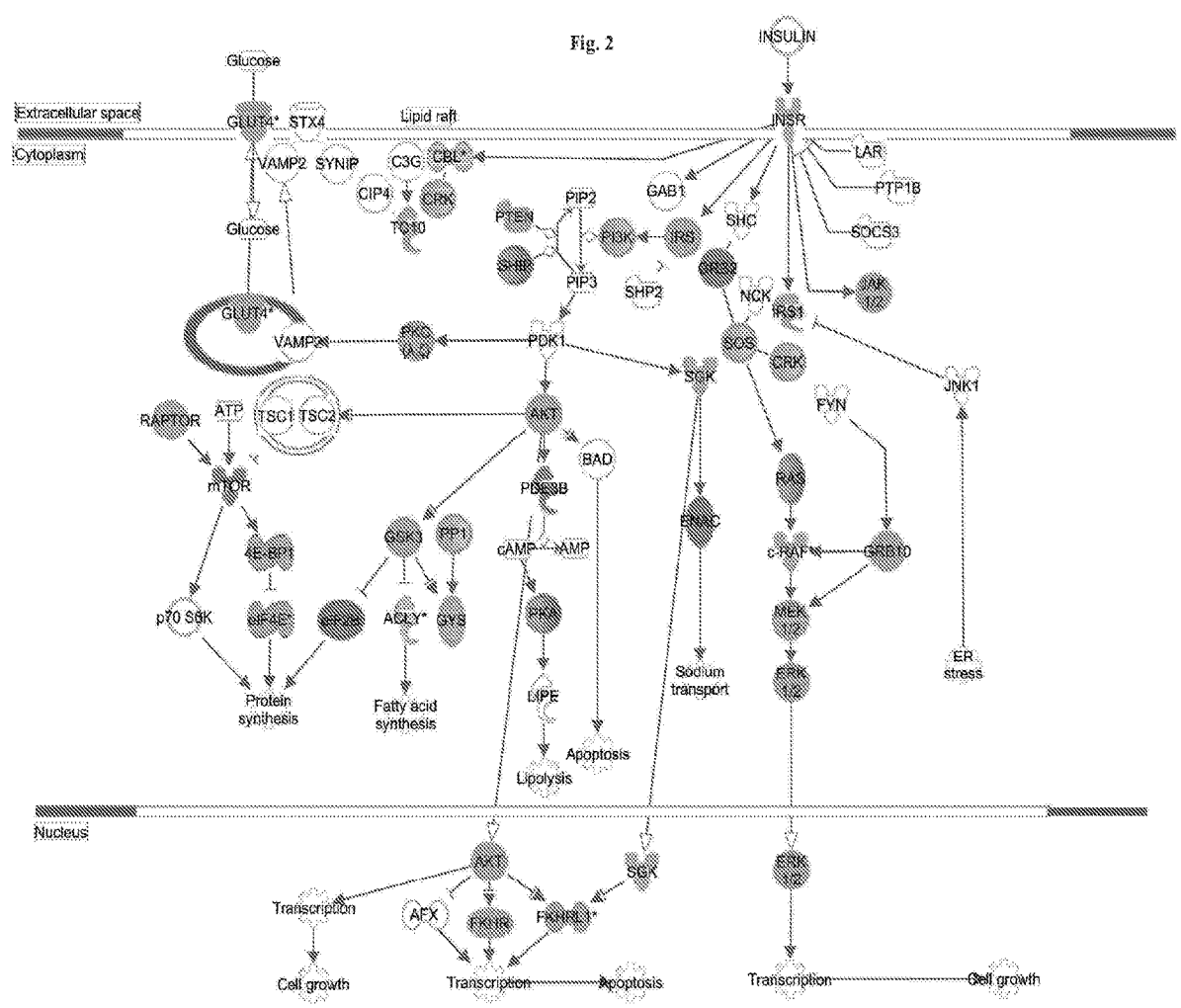
FIG. 2 depicts mRNA Targets of microRNAs Correlated to Altered Insulin Resistance after Surgery. Green color indicates predicted negative correlation of mRNA transcripts (i.e. positive correlation of microRNAs) to HOMA change following surgery, while red color indicates the reverse relationship ($r>0$ for mRNA targets and $r<0$ for microRNAs). Genes in gray represent targets of multiple microRNAs that have different correlational directions in relation to HOMA change. Specific r values and microRNA-mRNA pairs are detailed in Table 2.
Figure 3A:
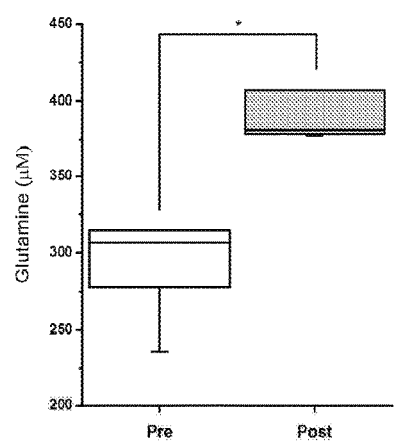
FIGS. 3A-3F depict Metabolite Changes One Year Following Gastric Bypass Surgery. Weight loss surgery produced a significant rise in fasting plasma Gln (FIG. 3A) and decrease in Glu (FIG. 3B). Plasma Glu/Gln ratio (FIG. 3C), branched chain amino acids (FIGS. 3D and 3E) all significantly decreased in obese patients following bariatric surgery, while glycine (FIG. 3F) increased post-surgery. All changes depicted are significant by ANCOVA at $p<0.05$.
Figure 3B:
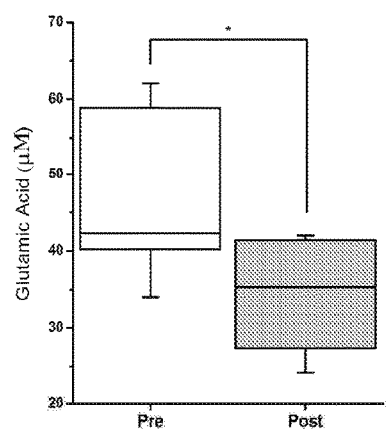
Figure 3C:
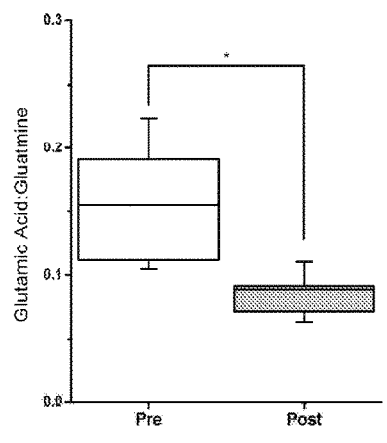
Figure 3D:
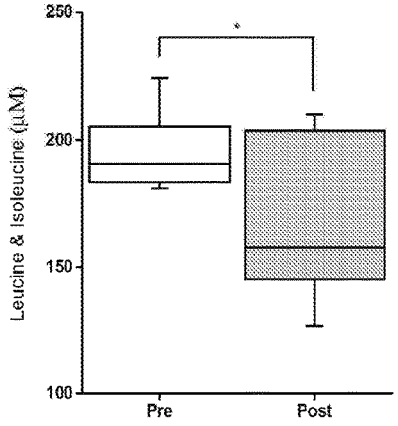
Figure 3E:
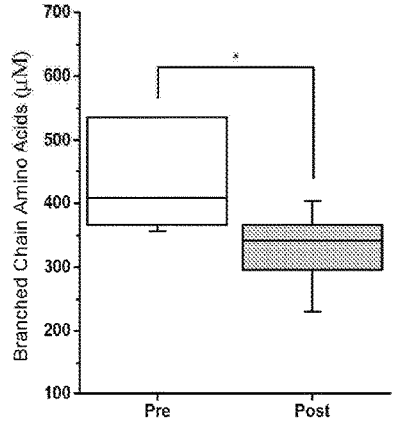
Figure 3F:
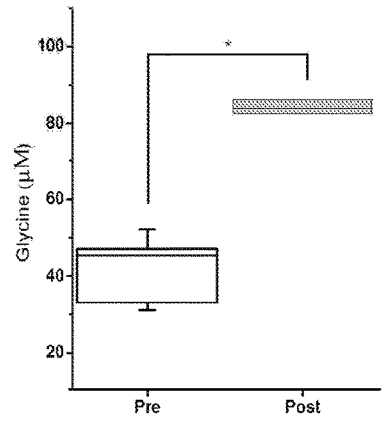
Figure 5A:
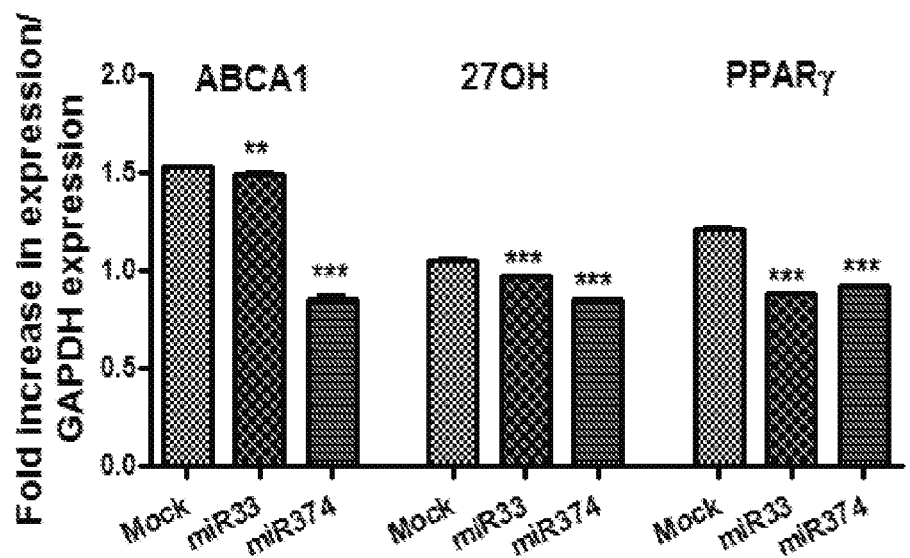
FIGS. 5A-B depict expression of cholesterol transport mRNA is decreased after over-expression of microRNA in human macrophages. Using microRNA mimic technology, miR33a and miR374b were introduced into THP-1 human macrophages.
Figure 5B:
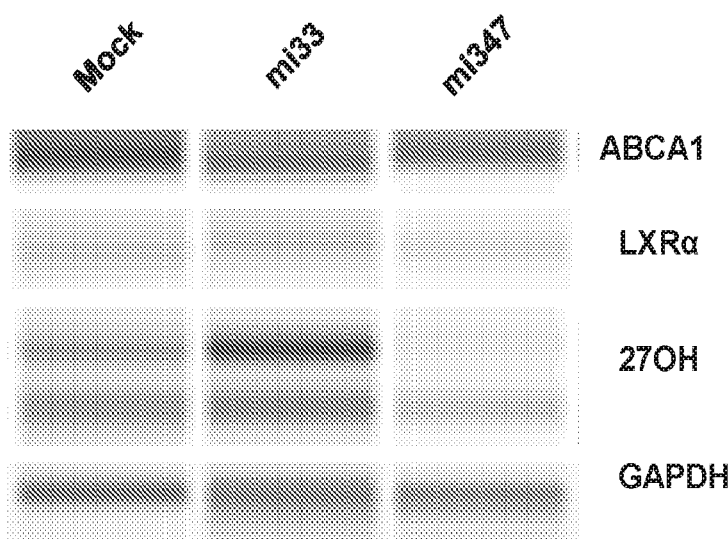

Recent reports indicated that miR-33 controls cholesterol homeostasis and targets ABCA1 and ABCG1 in vivo. See Rayner, K. J., et al., "Antagonism of miR-33 in mice promotes reverse cholesterol transport and regression of atherosclerosis," *J Clin Invest,* 2011. 121(7): p. 2921-31; and Horie, T., et al., "MicroRNA-33 deficiency reduces the progression of atherosclerotic plaque in ApoE−/− mice," *Journal of the American Heart Association,* 2012. 1(6): p. e003376; the disclosures of which are incorporated herein by reference in their entirety. Therefore, the effect of the microRNAs identified with miRTarVis on cholesterol efflux in human THP-1 macrophages was tested. Using microRNA mimic technology, miR-33a or miR-374b in macrophages was overexpressed and the expression of cholesterol efflux genes analyzed (FIG. 2). Decreased mRNA expression for the efflux proteins (i.e. ABCA1, 27-hydroxylase) and transcription factors (i.e. PPARγ and LXRα) after over-expression of these microRNAs was observed (see FIGS. 5A-5B).

Example 5

Asthma

Obesity is a major risk factor for difficult-to-control asthma, in which patients experience worse clinical control, poorer quality of life, reduced lung function, and poor responses to corticosteroids. Obese visceral adipose-derived exosomes were reported to contain microRNAs that are capable of impairing TGF-β signaling, an important pathway involved in the progression of airway remodeling, a component in asthma that is associated with poor clinical outcomes and lung function decline. Therefore, the present study investigated whether the association of adipose-derived exosomal microRNAs from obese youth with asthma was associated with poor asthma control.

Subjects in the AsthMaP-2 cohort (youth with physician-diagnosed asthma) were selected at the extremes of obesity (n=10) and leanness (n=10), matching for age and sex. Total exosomal RNA from adipose-derived exosomes isolated from both serum and urine were profiled. Significant correlations ($p \leq 0.05$) between obese adipose-derived exosomal microRNAs and Asthma Control Test (ACT) scores were found. Ingenuity Pathway Analysis generated predicted mRNA targets and representative signaling pathways.

Selected obese subjects had a BMI≥98$^{th}$ percentile and lean subjects had a BMI≤13$^{th}$ percentile for age and sex. Serum adipose-derived exosomes contained 12 ACT-correlated microRNAs predicted to target 2,963 mRNAs for which TGF-β Signaling was the top canonical pathway (ratio=36/87; $p=3 \times 10^{-9}$). Urinary adipose-derived exosomes contained 7 ACT-correlated microRNAs predicted to target 2,387 mRNAs for which TGF-β signaling was among the top canonical pathways (ratio=18/87; p=0.01). Specifically, the serum exosomal microRNAs were predicted to target the following TGF-β signaling mediators' mRNAs: downregulation of ACVR2B, SMAD3, SMAD5, and SMAD7 by miR-15a-5p (Fold Change (FC)=1.5; p=0.039) and upregulation of TGFB2 and TGFBR2 by miR-153-3p (FC=−1.7; p=0.041). While the urinary exosomal microRNAs were also predicted to target a similar set of TGF-β signaling mediators' mRNAs, the net effects were in the opposite direction: upregulation of ACVR2B and SMAD4 by miR-138-5p (FC=−1.2; p=0.033) and downregulation of TGFB2 and TGFBR2 by miR-153-3p (FC=1.6; p=0.026) and SMAD6 by miR-3187-5p (FC=2.3; p=0.008).

Poor asthma control in obese youths was associated with adipose-derived exosomal microRNAs in both serum and urine. In particular, those that were predicted to affect TGF-β signaling.

Summary of Examples 3-5

The bariatric surgery data showed that the microRNA content of circulating adipocyte-derived exosomes isolated from the peripheral blood, using e novel techniques of the present invention, were significantly modified following gastric bypass bariatric surgery and these changes correlated to improvements in insulin resistance post-surgery. Furthermore, we show that the altered microRNAs targeted a myriad of members in the insulin receptor signaling pathway. The macrophage data showed that exosomes from obese, but not lean, patients were functional and induced drastic changes in cholesterol efflux. Impaired cholesterol efflux in macrophages led to foam cell development and eventually atherosclerotic plaques in blood vessels. Finally, there was a difference between adipocyte-derived exosomes isolated from blood and urine (using our novel techniques described herein), which underscored the need for both isolation methods.

Example 6

Experimental Methods

Circulating Adipocyte-Derived Exosome Isolation:

Fatty acid binding protein 4 (FABP4) was used as a sensitive and specific marker for adipocyte-derived exosomes from plasma and serum samples. See Shan, T., W. Liu, and S. Kuang. (FASEB J, 2013. 27(1): p. 277-87, the disclosure of which is herein incorporated by reference in its entirety). Commercially-available antibody complexes and dextran-coated magnetic particles (StemCell Technologies, Vancouver, BC, Canada) were used to target FABP4+ exosomes in plasma and serum. The anti-FABP4-antibody complexes link targeted exosomes to magnetic particles. Labeled exosomes were then pulled to the sides of the tube when the sample was placed in a magnet. Magnetically-labeled exosomes remained in the tube while other exosomes were poured off into a new tube. The exosomes were then prepared for RNA studies as described below.

RNA Extraction and Amplification:

Adipocyte-exosomal total RNA was extracted using mirVana microRNA Isolation Kits (Life Technologies) and amplified total RNA with the Complete Seramir Exosome RNA Amplification Kit from Media and Urine (System Biosciences, Mountain View, Calif.) according to manufacturer's instructions. Agilent 2100 Bioanalyzer RNA Pico Chip (Agilent Technologies, Santa Clara, Calif.) was used to assess RNA quality at each step.

RNA Expression and Statistical Analyses:

RNA was labelled with Affymetrix® FlashTag™ Biotin HSR RNA Labeling Kit (Affymetrix, Santa Clara, Calif.) according to standard procedures. Labeled RNA was hybridized to Affymetrix GeneChip microRNA 4.0 arrays and run using a Fluidics Station 450 Protocol (FS450_002) (Affymetrix, Santa Clara, Calif.).

Resulting data were analyzed in Expression Console using RMA+DMBG (Affymetrix) and then exported to Partek Genomics Suite for analyses. Only mature human microRNAs were retained for statistical comparison between groups. Repeated measures ANOVA (time) was used to compare microRNA expression from pre- to post-surgery, using p≤0.05 as a filter. Rather than use a False Discovery Rate on the initial microRNA dataset, all microRNAs that met the unadjusted p<0.05 cutoff were carried into biological pathway analysis and used more stringent cutoffs during the pathway identification process (as described below). The relationship between insulin resistance (HOMA) and microRNA changes from baseline to one year post-surgery was also assessed using Pearson correlation coefficients.

Biological Pathway Analyses:

microRNAs found to be differentially regulated from pre- to post-surgery were uploaded into Ingenuity Pathway Analysis Suite (Ingenuity Inc., Redwood City, Calif.) for further analyses. First, targets of microRNAs were determined using IPA's microRNA Target Filter, which identifies experimentally validated microRNA-mRNA interactions from TarBase, miRecords, and the peer-reviewed biomedical literature, as well as predicted microRNA-mRNA interactions from TargetScan. A conservative filter was used at this point, using only experimentally validated and highly conserved predicted mRNA targets for each microRNA. The mRNA targets were analyzed through to Core Pathway Analyses, which identified relationships among the mRNAs in the dataset. The p values represented by the pathway analyses reduced the risk of false positive findings from the original repeated measures ANOVA, as false positive findings occur at random, while pathways are created only using biologically related elements (i.e. non-random). Canonical pathways, novel networks and common upstream regulators were then queried for overlap with our differentially expressed microRNA gene target list.

The invention claimed is:

1. A method of treating atherosclerosis and/or type 2 diabetes mellitus in a subject comprising
obtaining a biological sample from a subject which contains adipocyte-derived exosomes,
isolating adipocyte-derived exosomes from the biological sample using an anti-Fatty Acid Binding Protein 4 (FABP4) antibody or an antigen-binding fragment thereof,
measuring the amount of at least one microRNA present in the isolated adipocyte-derived exosomes, wherein at least one microRNA is selected from the group consisting of miR-33a, miR-10b, miR-20a, miR-374b, miR-504, and miR-101-1, and wherein an increase in the amount of the microRNA in the isolated adipocyte-derived exosomes from the subject relative to the amount of the microRNA in adipocyte-derived exosomes from a control subject indicates the subject has atherosclerosis and/or type 2 diabetes mellitus, and
administering a therapy to the subject for the atherosclerosis and/or type 2 diabetes mellitus, wherein said therapy is the administration of a cholesterol or glucose lowering agent or a statin to the subject.

2. The method of claim 1,
wherein said subject is a human subject, and
wherein the biological sample is blood, serum or urine.

3. The method of claim 1, wherein the anti-FABP4 antibody or an antigen-binding fragment thereof is conjugated to magnetic beads.

4. The method of claim 1, wherein said therapy comprises administering a cholesterol lowering agent selected from the group consisting of simvastatin, nicotinic acid, cholestyramine, colestipol, probucol, clofibrate, gemfibrozil, fenofibrate, and ciprofibrate, to the subject.

5. The method of claim 1, wherein said subject has type 2 diabetes mellitus and said therapy is the administration of a glucose lowering agent to the subject.

6. The method of claim 5, wherein said glucose lowering agent is selected from the group consisting of orlistat, lorcaserin, phentermine, liraglutide, insulin, amylin, leptin, glucagon, glucagon-like peptide (GLP-1), glucagon-like peptide (GLP-1) receptor agonist, a sulfonylurea, a biguanide, somatostatin, diazoxide, a sodium-glucose co-transporter 2 (SGLT-2) inhibitor, acarbose, miglitol, a dopamine agonist, a dipeptidyl peptidase 4 (DPP-4) inhibitor, a meglitinide, an alpha-glucosidase inhibitor, and a thiazolidinedione.

* * * * *